United States Patent

Navab

[11] Patent Number: 5,930,329
[45] Date of Patent: Jul. 27, 1999

[54] APPARATUS AND METHOD FOR DETECTION AND LOCALIZATION OF A BIOPSY NEEDLE OR SIMILAR SURGICAL TOOL IN A RADIOGRAPHIC IMAGE

[75] Inventor: Nassir Navab, Plainsboro, N.J.

[73] Assignee: Siemens Corporate Research, Inc., Princeton, N.J.

[21] Appl. No.: 08/935,269

[22] Filed: Sep. 22, 1997

[51] Int. Cl.⁶ .................................................. G01N 23/04
[52] U.S. Cl. ........................................ 378/98.12; 600/424
[58] Field of Search ................................ 378/62, 98, 12; 600/424

[56] References Cited

U.S. PATENT DOCUMENTS

| | | | |
|---|---|---|---|
| 4,626,908 | 12/1986 | Tani | 378/98.12 |
| 5,810,728 | 9/1998 | Kuhn | 600/410 |

Primary Examiner—David P. Porta
Assistant Examiner—David Vernon Bruce
Attorney, Agent, or Firm—Adel A. Ahmed

[57] ABSTRACT

A method for the detection and localization of a surgical tool in a radiographic image, including an image of a surgical device and an anatomical background image, includes the steps of generating a radiographic reference image, including an image of a surgical device and an anatomical background image and applying an oscillating movement to the device. The method further includes the steps of generating a number k of radiographic images during the oscillating movement; subtracting each image from the reference image, so as to generate a difference image; and deriving the mathematical intersection of all of the reference images, whereby a resulting image results including only the image of the device on the radiographic reference image and substantially without the anatomical background image.

18 Claims, 22 Drawing Sheets

APPARATUS AND METHOD FOR DETECTION AND LOCALIZATION OF A BIOPSY NEEDLE OR SIMILAR SURGICAL TOOL IN A RADIOGRAPHIC IMAGE

The present invention relates to an apparatus and method for detection and localization of a biopsy needle or similar surgical tool in a radiographic image produced by an imaging device, and more particularly to facilitating the accurate detection of the position of a surgical tool, such as a biopsy needle or device when such needle or device is overlaid with anatomical background in radiographic images on the screen of a fluoroscope or the like display instrument.

Needle biopsy is one of the most frequent surgical interventions. Typically, a fine needle is used to remove tissue portions from a lesion inside the body. If the lesion is very small and is deep-seated within the body or is not palpable, the surgeon needs guidance in order to make sure that the tip of the needle reaches the desired location.

Currently used image based guidance methods include the following. Ultrasound (US), X-ray fluoroscopy, CT fluoroscopy, and CT/MRI in combination with real time registration tools. The first three methods provide real time intra-operative images of the patient and enable the surgeon to see the needle as it approaches the target. Ultrasound is relatively inexpensive and is a readily available image modality. However, its usage for guidance is limited to lesions that are close to the skin and that show a well defined signal.

The X-ray fluoroscope is a widely available, low cost two-dimensional (2D) imaging equipment. Since it shows a two-dimensional projection, two (generally orthogonal) views are necessary in order to determine the biopsy needle position. This can be done by turning the arm of a simple fluoroscope, such as a C-arm fluoroscope, an example of which is shown in FIG. 1, or by using a fluoroscope such as that illustrated in FIG. 2 that provides two simultaneous orthogonal views. Since the needle has to be manipulated in the image field, one cannot avoid an X-ray exposure of the physician when using such techniques. As is well-known, unnecessary exposure of health workers to X-ray radiation is believed to be hazardous to health and it is desirable that it should be avoided to the extent possible.

CT-Fluoroscopy permits real-time display of CT images. The physician controls X-ray exposure during continuous tube rotation. The exact position of the needle can be traced by moving the table. In the case for CT-Fluoroscopy also, the surgeon is exposed to X-rays.

CT/MRI in combination with real time registration tools is based on pre-operative 3-D data acquisition (CT or MRI). The lesion is outlined in the resulting dataset. During the actual biopsy, the position and orientation of the patient and the needle have to be known precisely and aligned with the pre-operative data.

Therefore two registrations have to be used for guiding the needle: the pre-operative data showing the lesion has to be registered with the patient. This can be done by attaching invariant markers to the patient (stereo-tactic frames) before data acquisition or by matching invariant patient features, such as the skull or bones.

The needle has to be registered with the patient. One possibility is to attach optical markers to the needle which can be tracked by a system of cameras or by X-ray fluoroscopy, or to use mechanical devices like passive robot arms that register the position of the needle at any moment. This technique requires highly specialized and costly 3-D imaging facilities that are typically only available at a few research sites. Despite the image guidance, a successful biopsy procedure still depends on the manual skills and judgement of the surgeon who is manipulating the needle.

There is a need for an alignment device that is adjustable to the right direction and that indicates the distance to a deep-seated target. Among the benefits that result from such a device are acceleration of the procedure, increase of the safety of the procedure, and reduction of radiation exposure for both the patient and for the surgeon.

In an application for patent entitled APPARATUS AND METHOD FOR DETERMINING THE CORRECT INSERTION DEPTH FOR A BIOPSY NEEDLE and TRIGONOMETRIC DEPTH GAUGE FOR BIOPSY NEEDLE, which is more completely referenced below, there is described an apparatus for determining a proper insertion depth of a biopsy needle to be inserted at a selected point on the body of a patient so that a sampling end of the needle just reaches to a designated target area within the body. Briefly, the apparatus disclosed in the above-mentioned patent application to Navab et al., comprises at least one straight calibrated pointing device aligned to point through the selected point in a straight line passing through the designated target region, the pointing device exhibiting first and second markers along its length such that respective images are formed on a first image plane by utilizing radiation from a radiation source, along with images corresponding to the selected point and the target area, the images being formed along a straight line in this order: (A) the first marker, (B) the second marker, (C) the selected point, and (D) the target region. The apparatus includes an arrangement for measuring distances on the image plane between images (A), (B), (C), and (D); and a calculator for calculating the cross ratio of the distances, whereby the proper insertion depth of the biopsy needle is determined. The disclosure of the above application is hereby incorporated by reference as background information for the present application to the extent it is not inconsistent therewith. Another related type of apparatus is disclosed in an application for patent entitled TRIGONOMETRIC DEPTH GAUGE FOR BIOPSY NEEDLE which is more completely referenced below.

In performing the method, it is important for the surgical practitioner to be able to obtain correct reading of the depth to which insertion is required and, to this end, it is necessary to be able to identify positively the surgical tool and image-opaque markers placed upon it in order to obtain the necessary data for accurate depth determination.

This is of particular importance when an automatic mode of operation is utilized, as will be further explained below. It becomes particularly difficult to make such identification of a surgical tool, such as a biopsy needle or other device, when the needle or device is overlaid with anatomical background as is so often the case in radiographic images on the screen of a fluoroscope or other imaging device.

Prior applications for U.S. Letters Patent in which the present inventor is a named inventor are of particular interest as background to the present application. The patent applications, whereof the disclosure is herein incorporated by reference to the extent not inconsistent with the present invention, are as follows. CALIBRATION APPARATUS FOR X-RAY GEOMETRY, in the names of Navab and Bani-Hashemi, filed Dec. 21, 1995, and accorded Ser. No. 08/576,736; CALIBRATION SYSTEM AND METHOD FOR X-RAY GEOMETRY, in the names of Nabab and Bani-Hashemi, filed Dec. 21, 1995, and accorded Ser. No. 08/576,718; APPARATUS AND METHOD FOR POSITIONING A BIOPSY NEEDLE, in the names of Navab and Geiger, filed Sep. 30, 1996, and accorded Ser. No. 08/722, 725; APPARATUS AND METHOD FOR POSITIONING A BIOPSY NEEDLE, in the names of Navab and Geiger, filed Sep. 30, 1996, and accorded Ser. No. 08/722,707; APPARATUS AND METHOD FOR DETERMINING THE CORRECT INSERTION DEPTH FOR A BIOPSY NEEDLE, in the names of Navab and Geiger, filed Sep. 30, 1996, and accorded Ser. No. 08/722,708; and TRIGONOMETRIC DEPTH GAUGE FOR BIOPSY NEEDLE, in the name of Geiger and Navab, and accorded Ser. No. 08/576,736, filed Dec. 21, 1995.

Drawings of the aforelisted patent applications are helpful to a fuller understanding of the present invention and are herein included to help illustrate an example of the background and environment in which the present invention can be used.

In accordance with an aspect of the invention, a method for detection and localization of a surgical tool in a radiographic image comprises the steps of: generating a radiographic reference image $I_p$, including an image of a surgical device and an anatomical background image; applying an oscillating movement to the device; generating a number k of radiographic images $I_k$ during the oscillating movement; subtracting each image $I_k$ from a preceding reference image $I_p$ so as to generate a difference image ($I_k-I_p$); and deriving the mathematical intersection of all of the reference images ($I_k-I_p$), whereby a resulting image results including only the image of the device on the radiographic reference image $I_p$ and substantially without the anatomical background image.

In accordance with another aspect of the invention, the steps of subtracting each image $I_k$ from the reference image $I_p$ and of deriving the mathematical intersection are performed on digitized versions of the respective images.

In accordance with another aspect of the invention, the step of generating a radiographic reference image $I_p$, including an image of a surgical device is carried out on a biopsy needle.

In accordance with another aspect of the invention, the step of applying an oscillating movement to the device is performed no faster than a rate at which acquisition can be effected of two successive distinct radiographic images of the surgical tool. 5. A method for detection and localization of a positioning device in a radiographic image in the presence of anatomical background images, comprising the steps of: generating a radiographic reference image $I_p$, including an image of the positioning device and an anatomical background image; applying an oscillating movement to the device; generating a number k of radiographic images $I_k$ during the oscillating movement; subtracting each image $I_k$ from a preceding reference image $I_p$ so as to generate a difference image ($I_k-I_p$); and deriving the mathematical intersection of all of the reference images ($I_k-I_p$), whereby a resulting image results including only the image of the device on the radiographic reference image $I_p$ and substantially without the anatomical background image.

In accordance with another aspect of the invention, apparatus for detection and localization of a positioning device in a radiographic image in the presence of anatomical background images comprises: apparatus for generating a radiographic reference image $I_p$, including an image of the positioning device and an anatomical background image; apparatus for applying an oscillating movement to the device; apparatus for generating a number k of radiographic images during $I_k$ the oscillating movement; apparatus for subtracting each image $I_k$ from a preceding reference image $I_p$ so as to generate a difference image ($I_{k-Ip}$); and apparatus for deriving the mathematical intersection of all of the reference images ($I_k-I_p$), whereby a resulting image results including only the image of the device on the radiographic reference image $I_p$ and substantially without the anatomical background image.

In accordance with another aspect of the invention, apparatus for tracking a positioning device in a sequence of consecutive radiographic images, the positioning device exhibiting a change of position from one radiographic image to the next, comprises: apparatus for generating a radiographic reference image $I_p$, including an image of a positioning device and an anatomical background image; apparatus for applying an oscillating movement to the device; apparatus for generating a number k of radiographic images during the oscillating movement; apparatus for subtracting each image $I_k$ from a preceding reference image $I_p$ so as to generate a difference image ($I_k-I_p$); and apparatus for deriving the mathematical intersection of all of the reference images ($I_k-I_p$), whereby a resulting image results including only the image of the device on the radiographic reference image $I_p$ and substantially without the anatomical background image.

In accordance with another aspect of the invention, apparatus for detection and localization of a surgical tool in a radiographic image, for use in conjunction with radiographic equipment or the like imaging equipment, comprising: apparatus for applying an oscillating movement $I_k$ to the device; apparatus for generating a radiographic reference image $I_p$, including an image of a surgical device and an anatomical background image, and for generating a number k of radiographic images during the oscillating movement; apparatus for subtracting each image $I_k$ from a preceding reference image $I_p$ so as to generate a difference image ($I_k-I_p$); and apparatus for deriving the mathematical intersection of all of the reference images ($I_k-I_p$).

The invention will be more fully understood from the detailed description of preferred embodiments, in conjunction with the drawing, not necessarily to scale, in which FIG. 1 shows a known type of C-arm fluoroscope, such as may be utilized in conjunction with the present invention;

Figure 4:
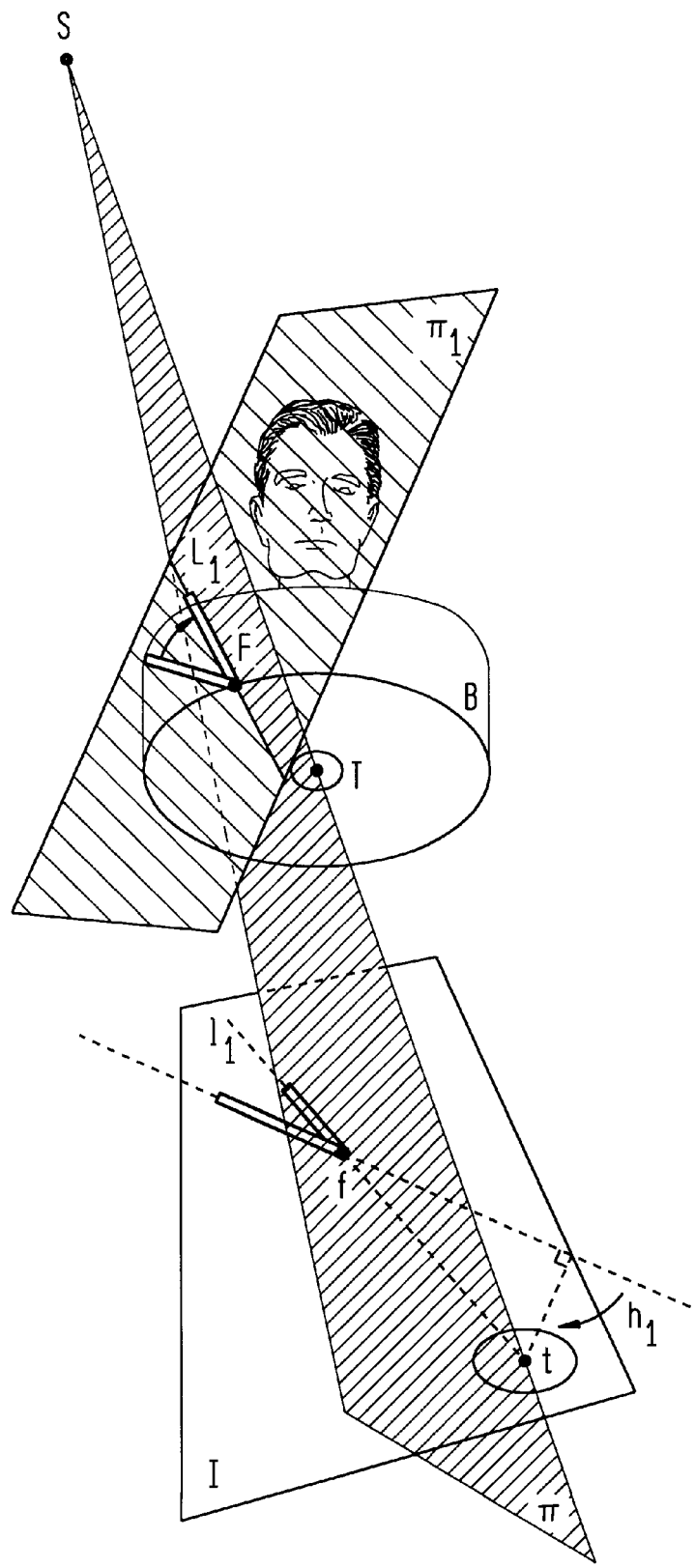
Figure 5:
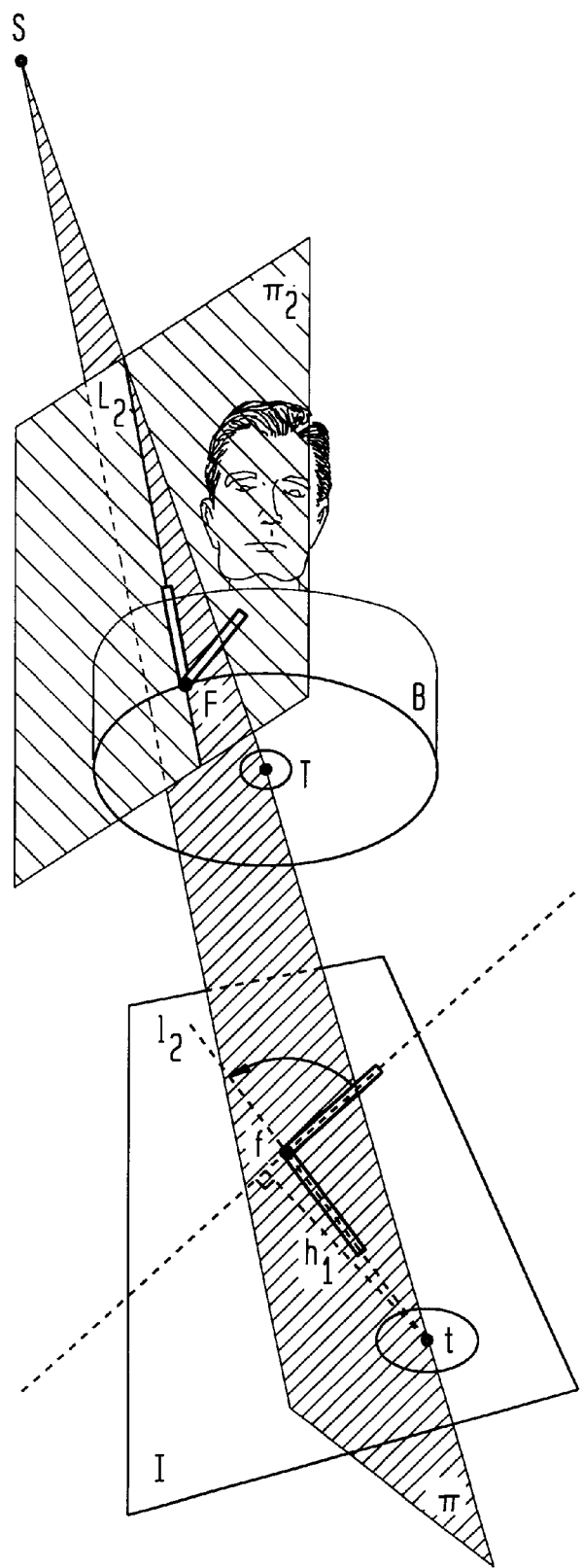
Figure 6:
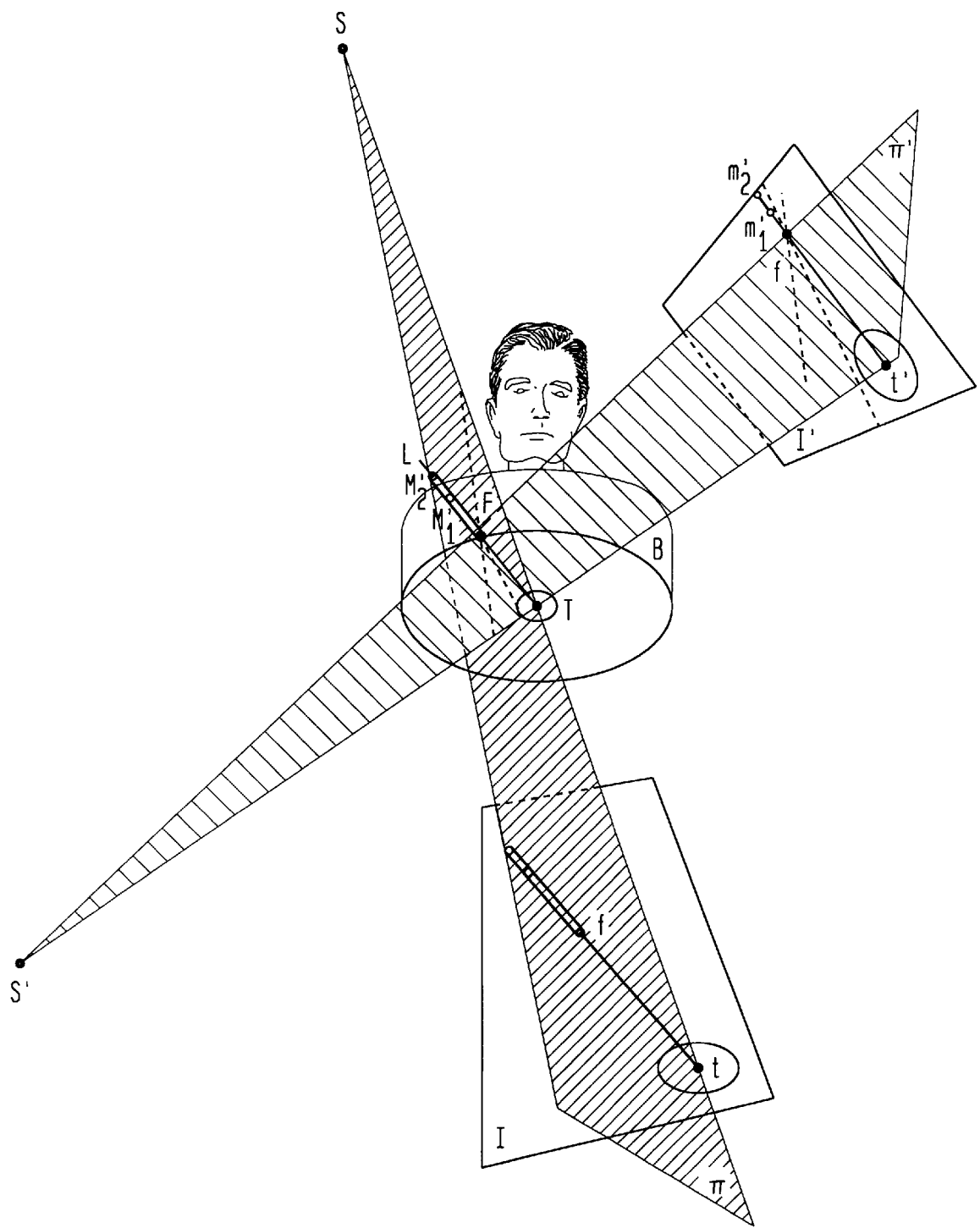
Figure 7:
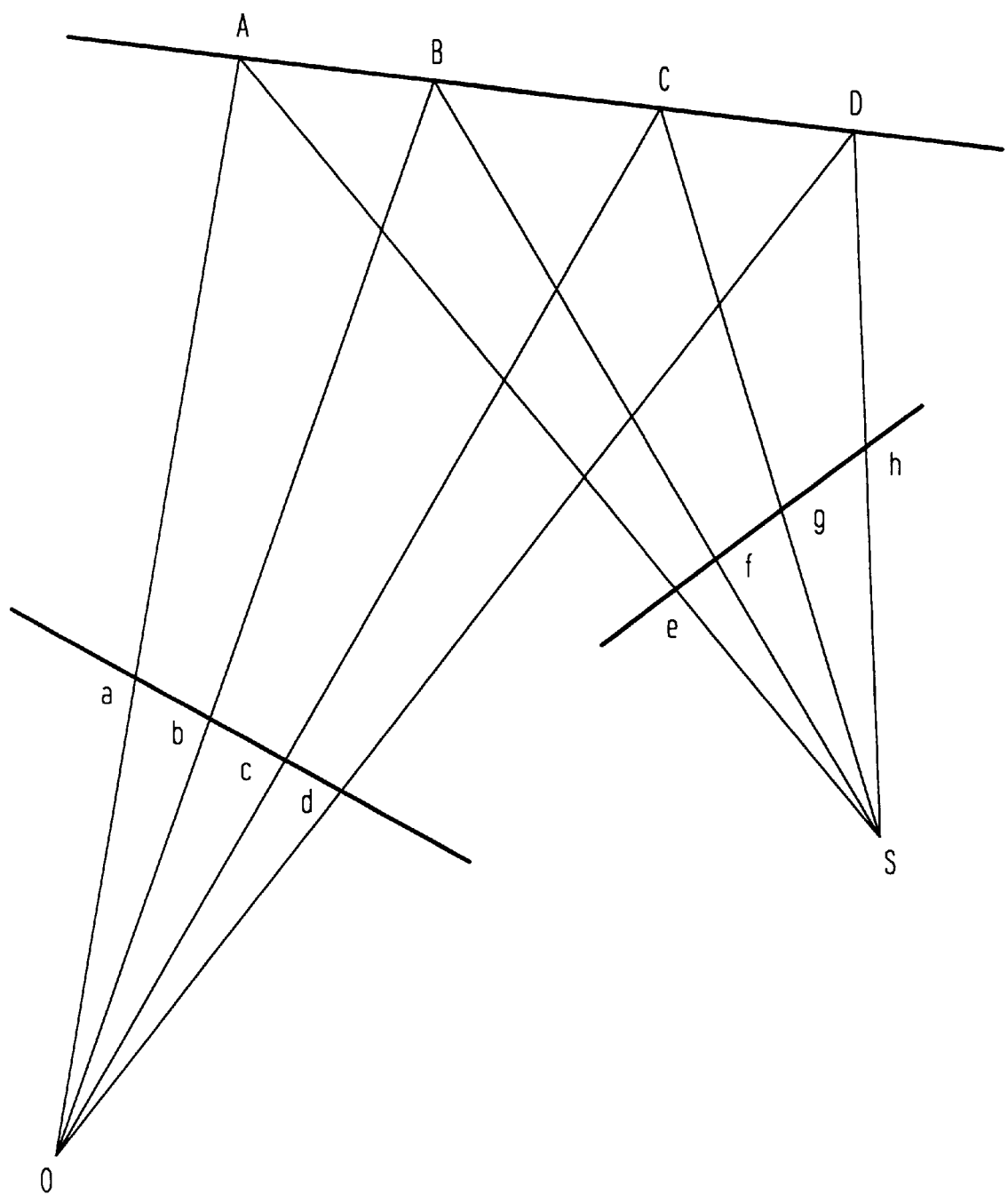
Figure 8:
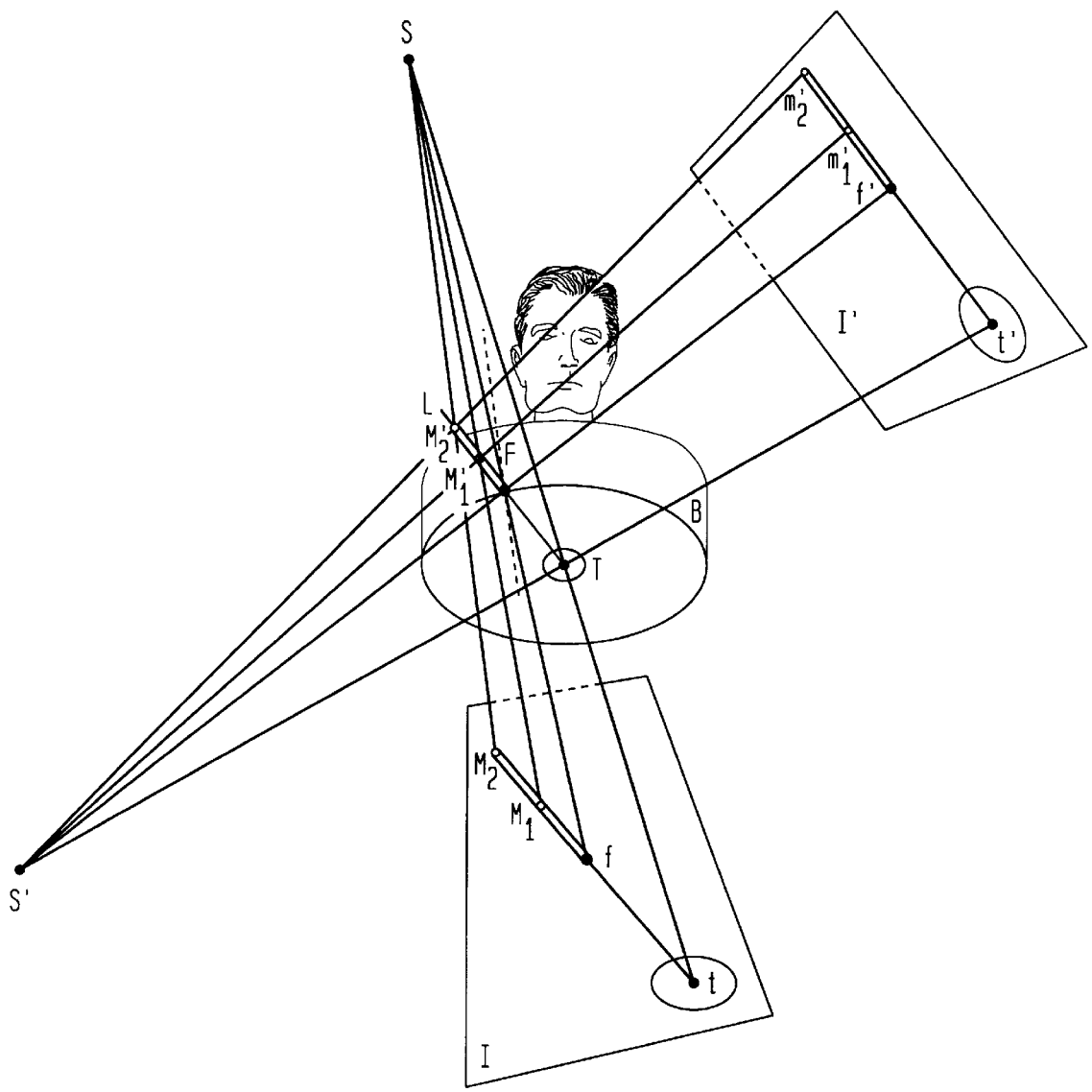
Figure 9:
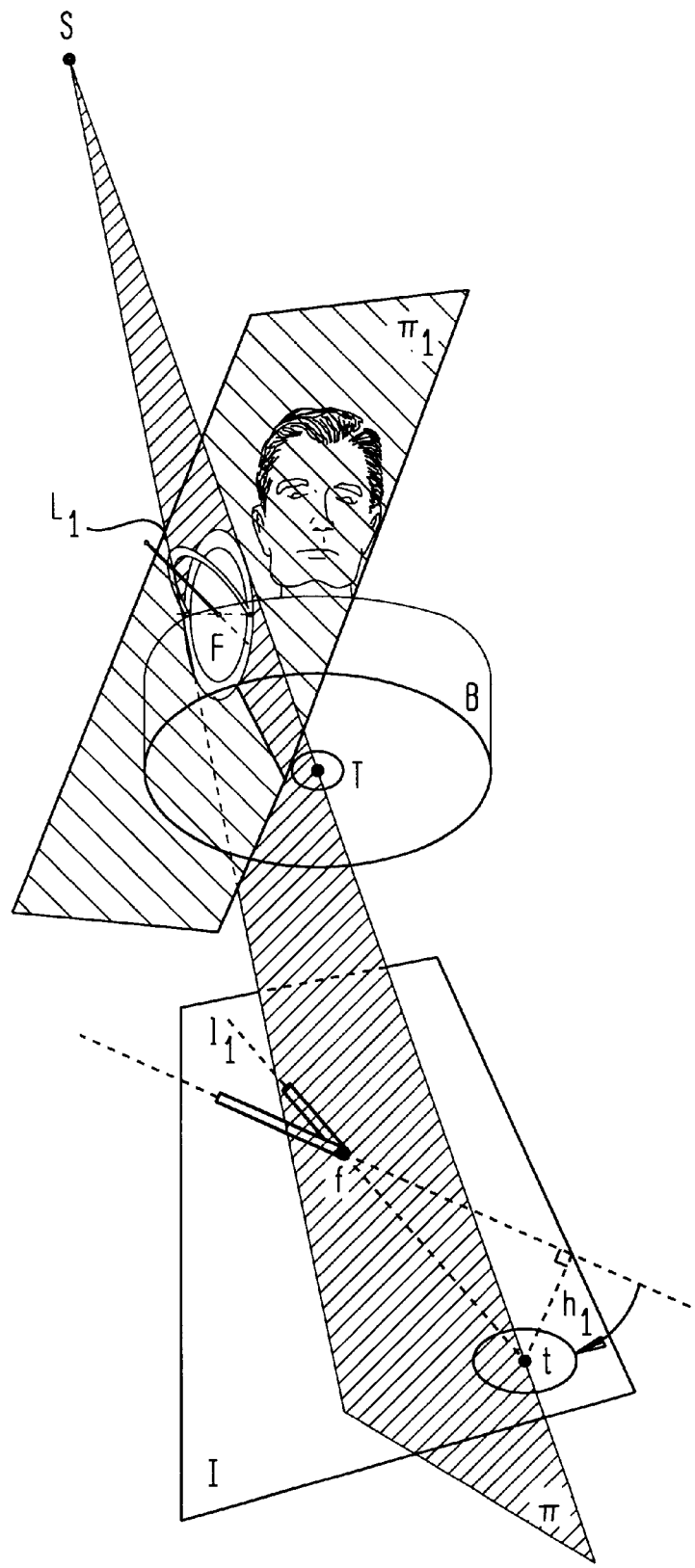
Figure 10:
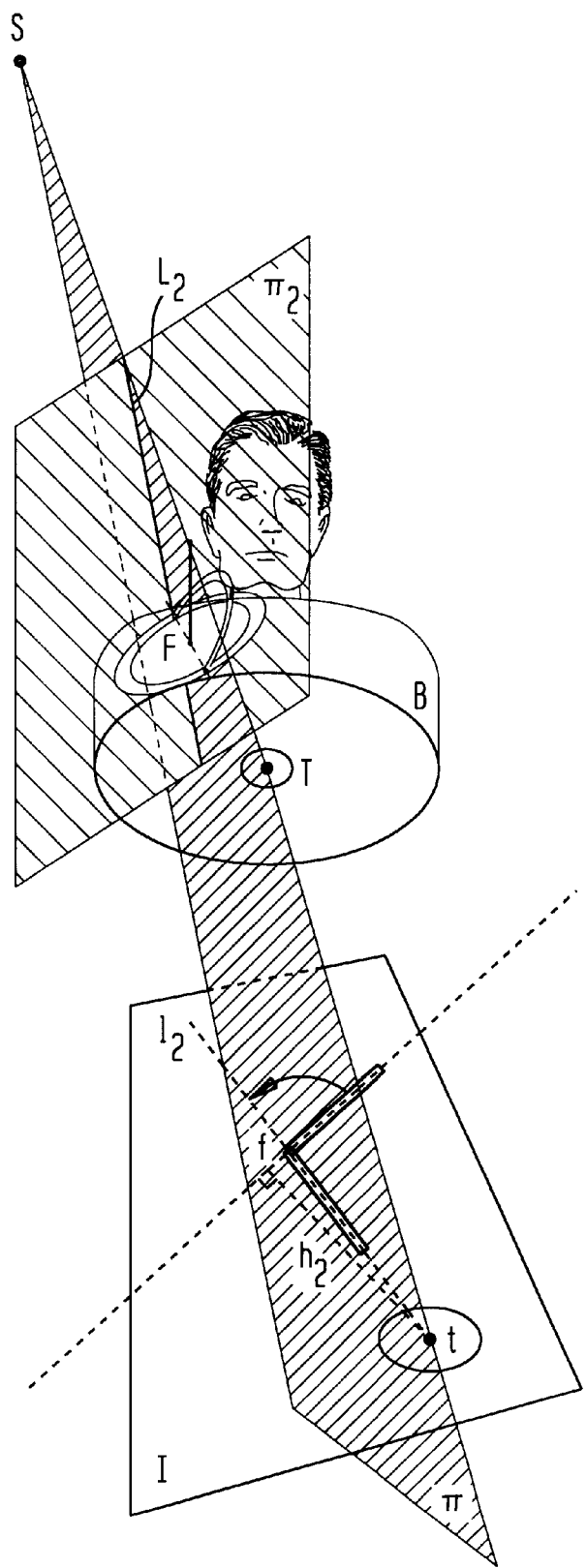
Figure 11:
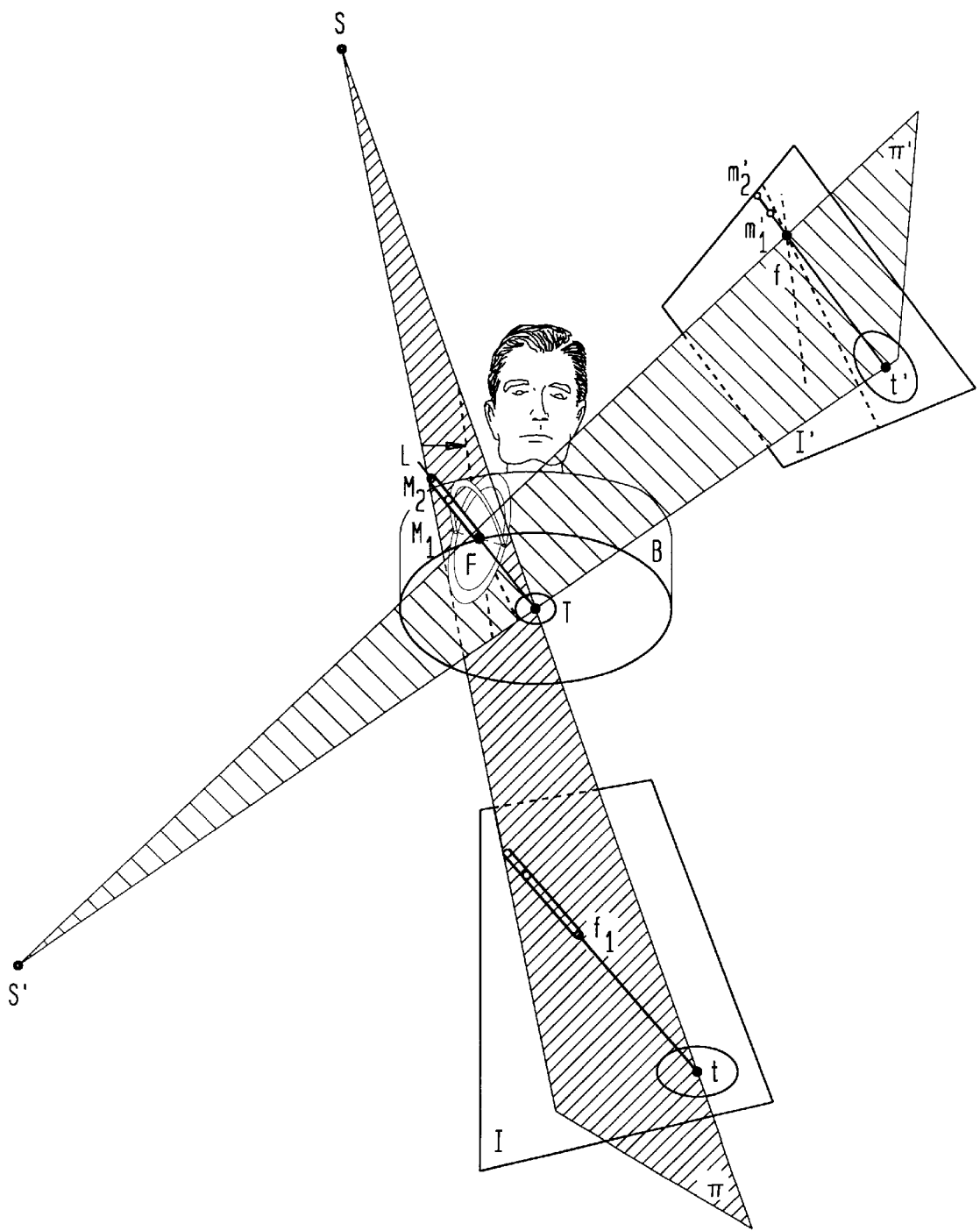
Figure 12:
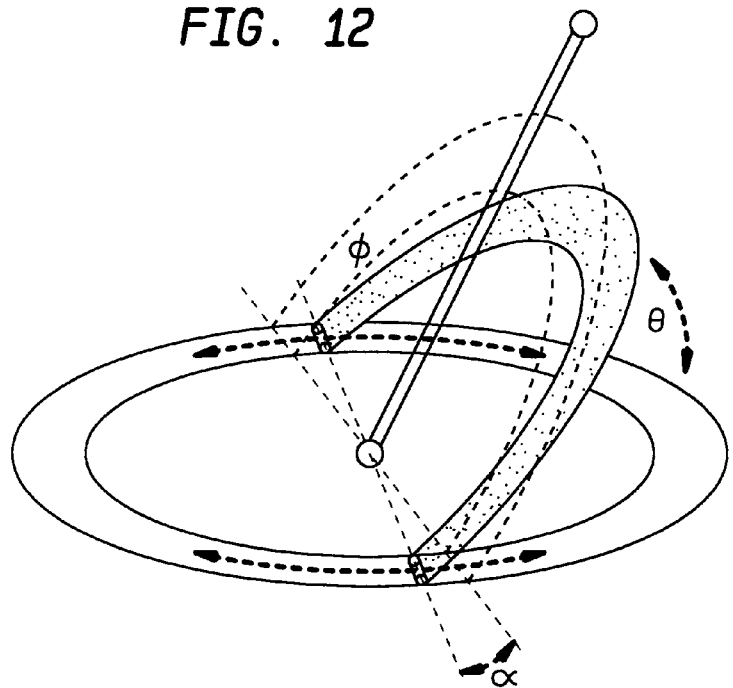
Figure 13:
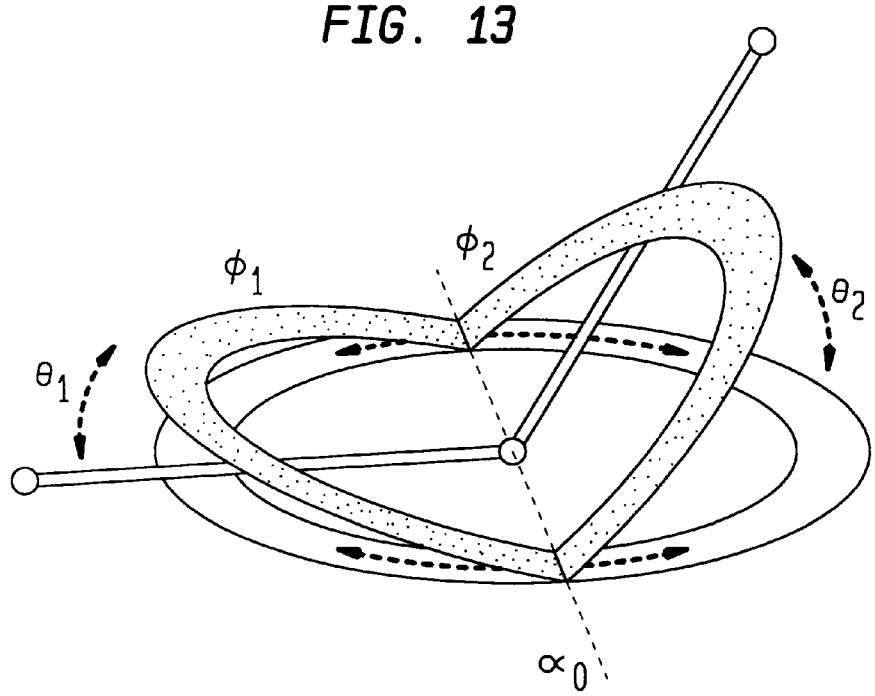
Figure 14:
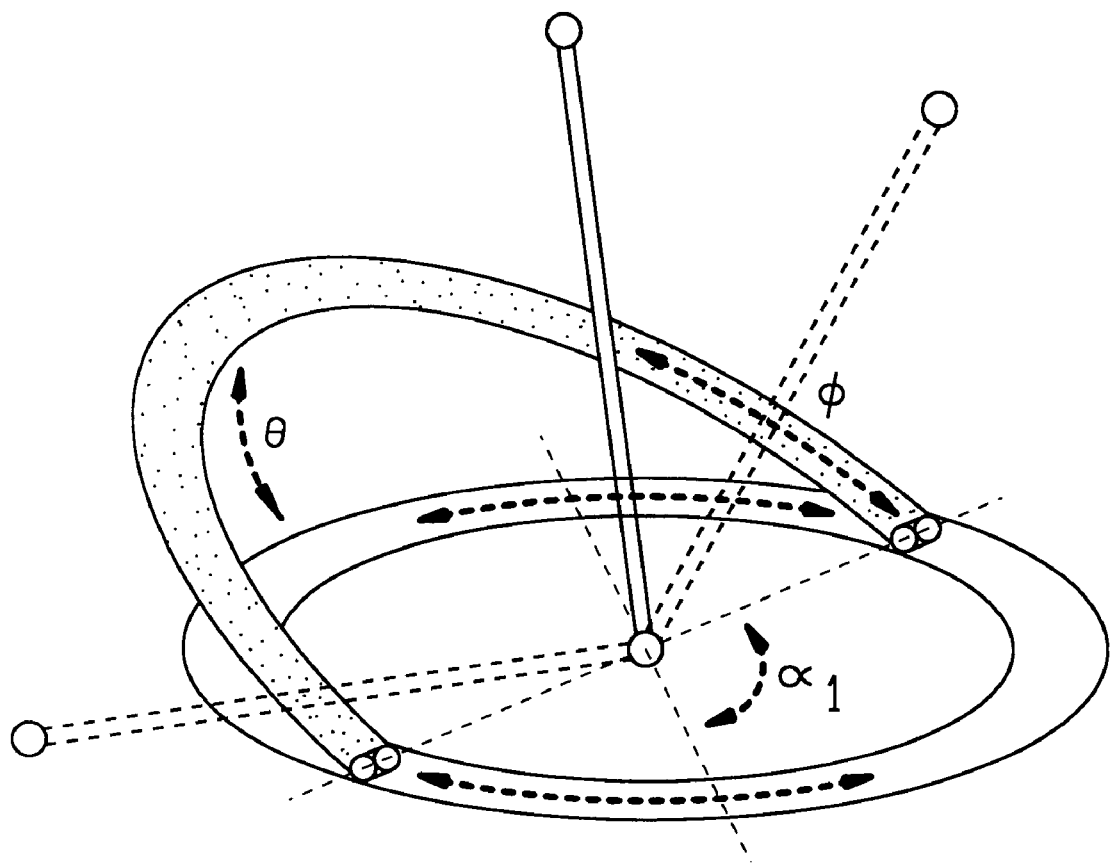
Figure 15:
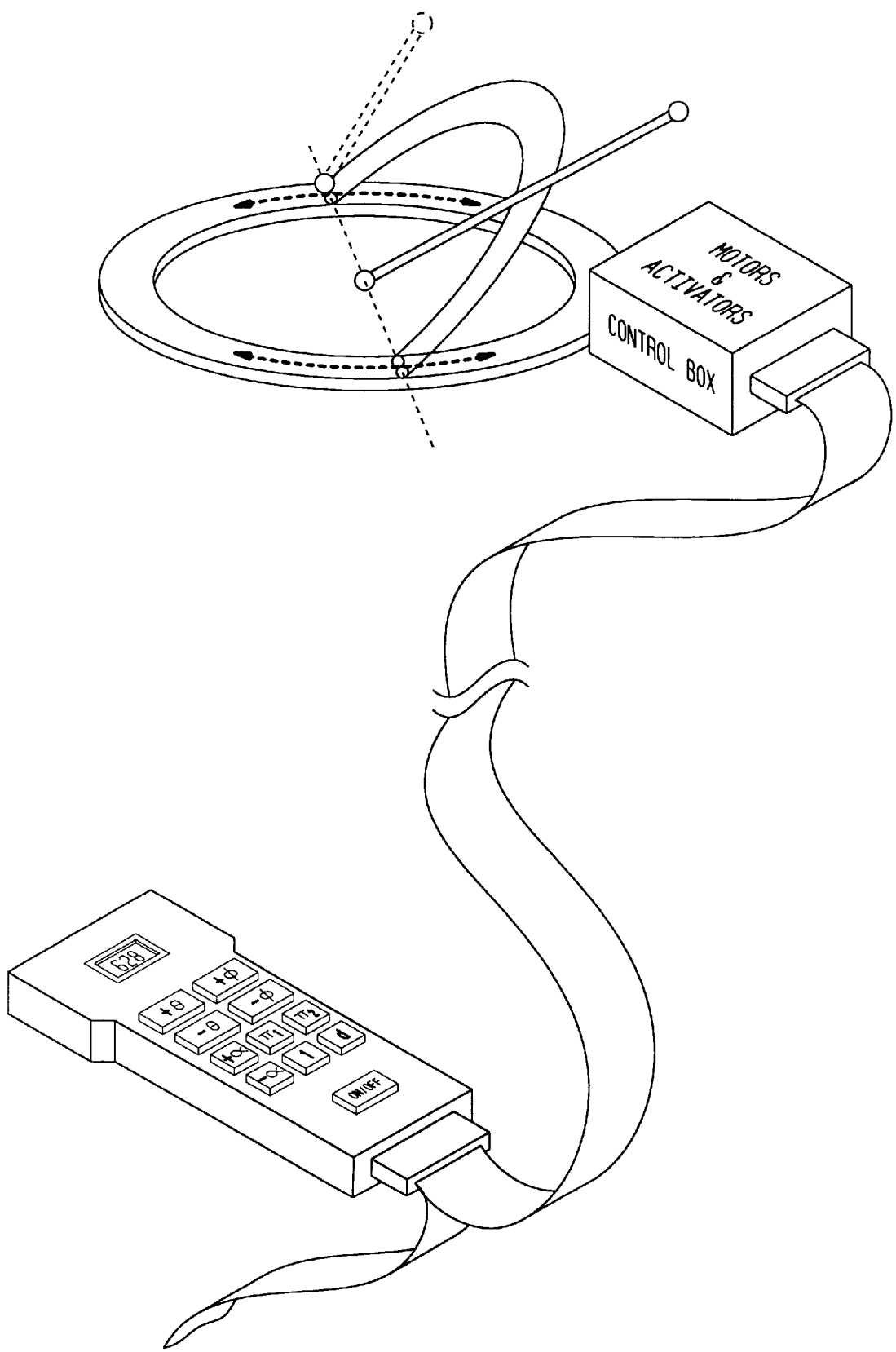
Figure 16:
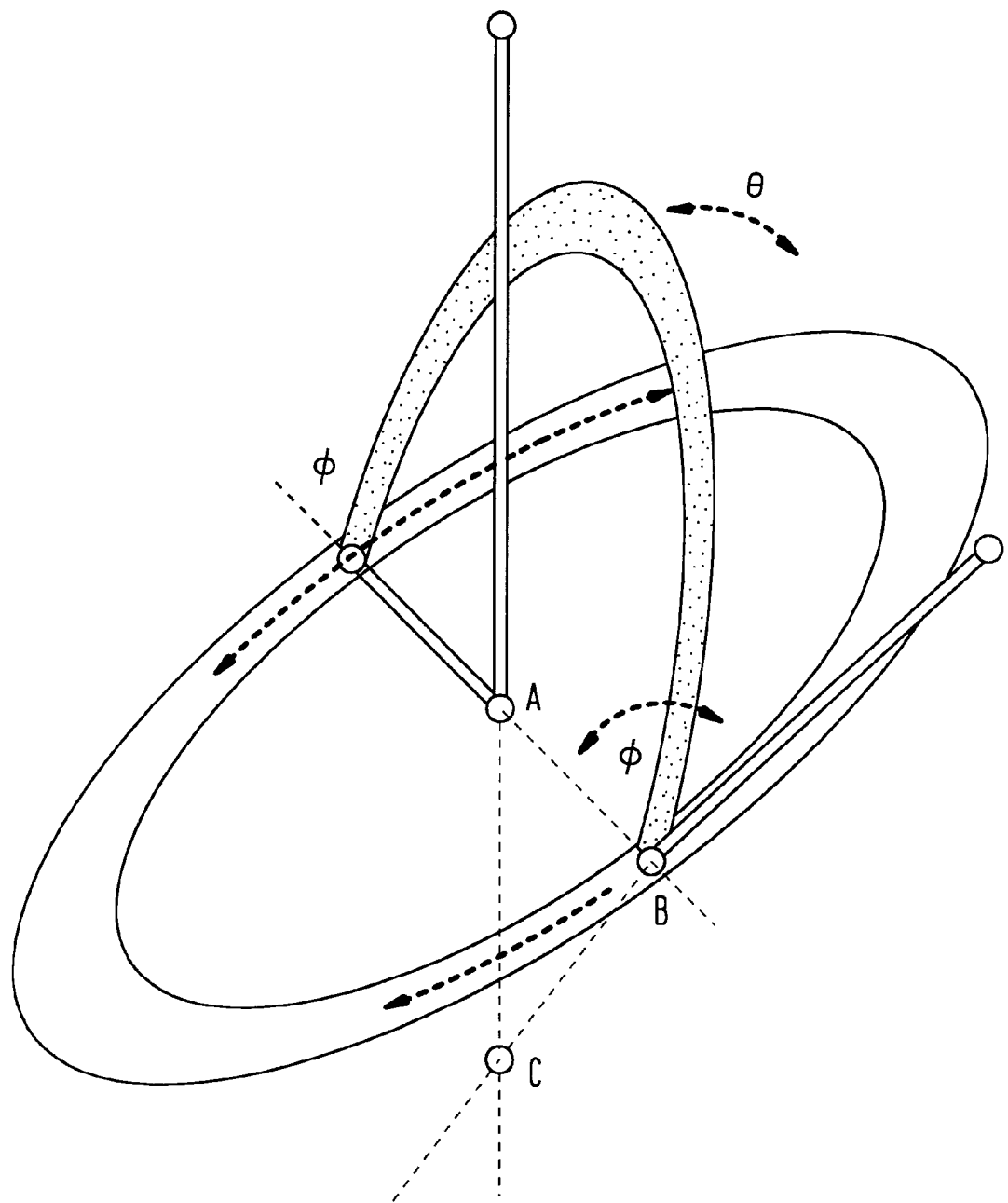
Figure 17:
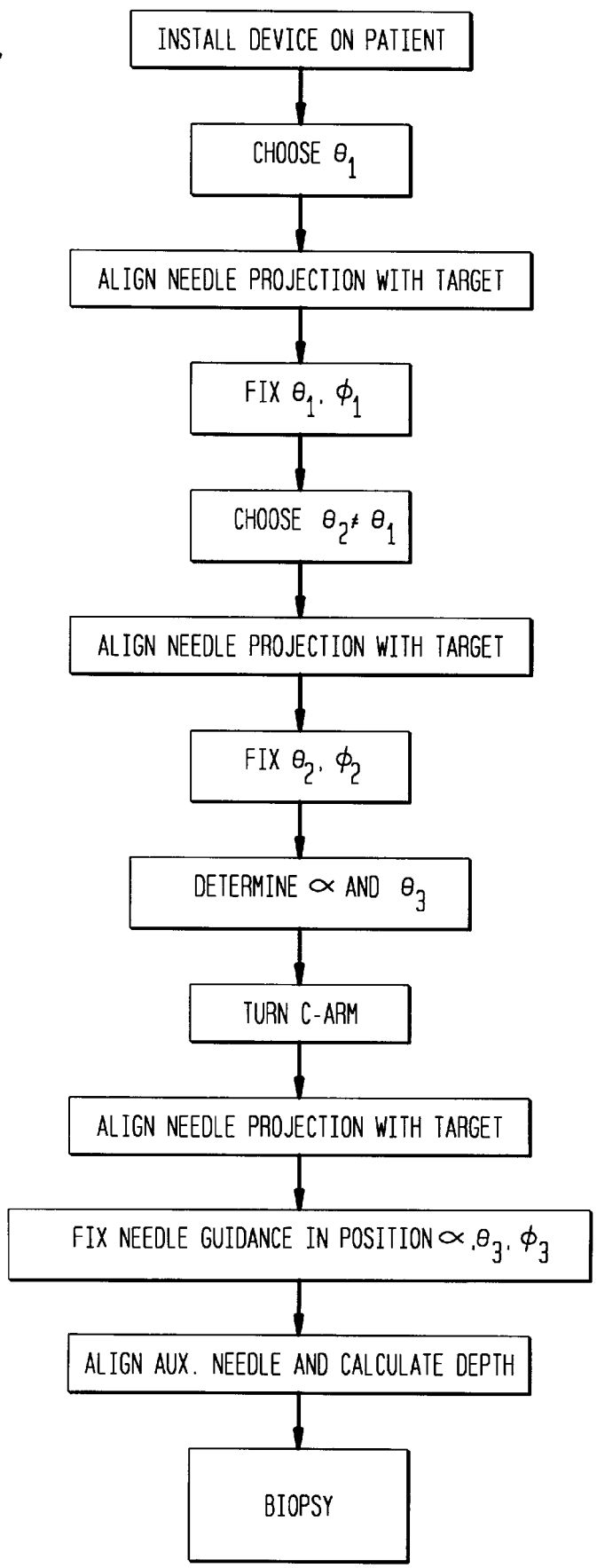
Figure 18:
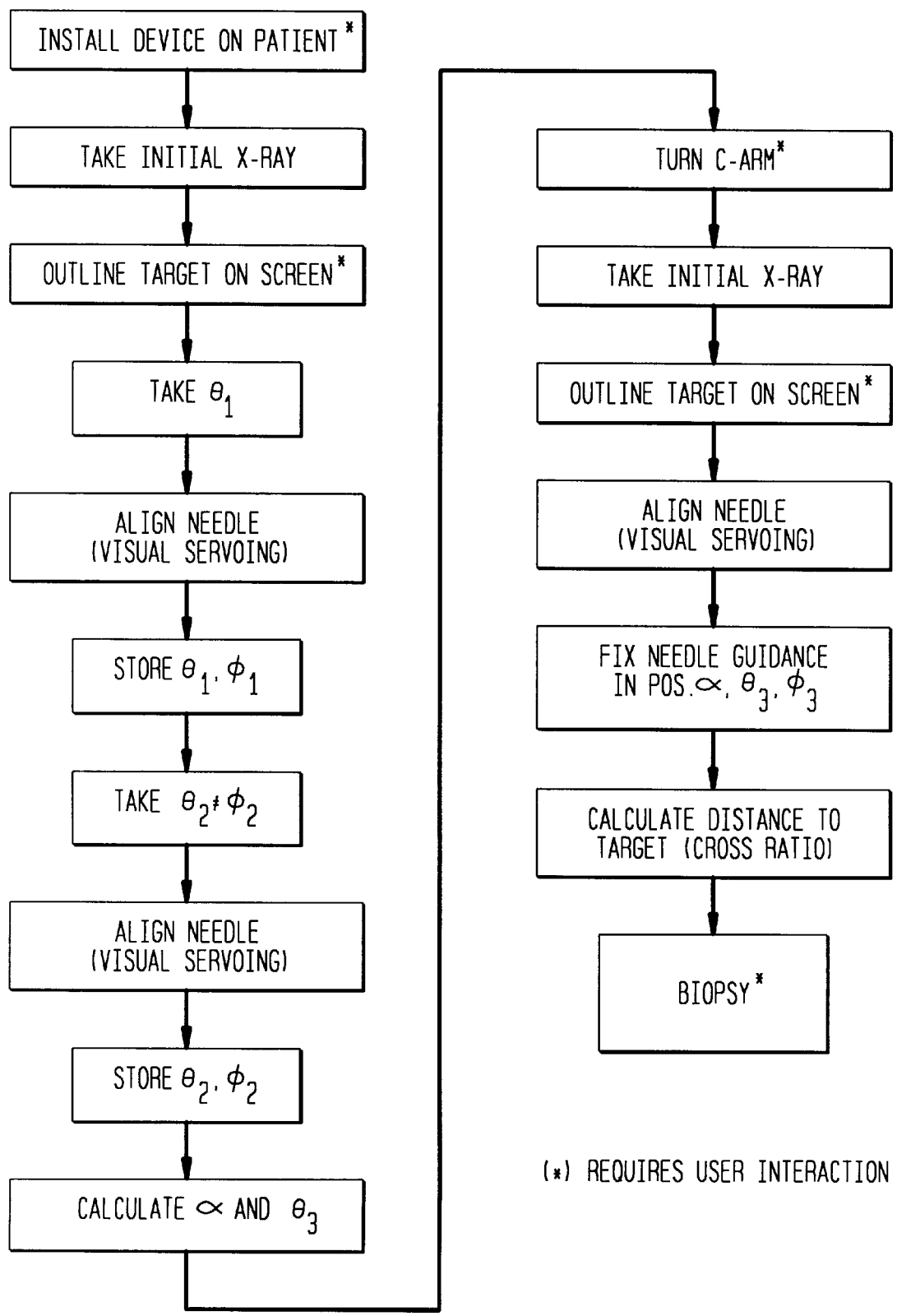
Figure 19:
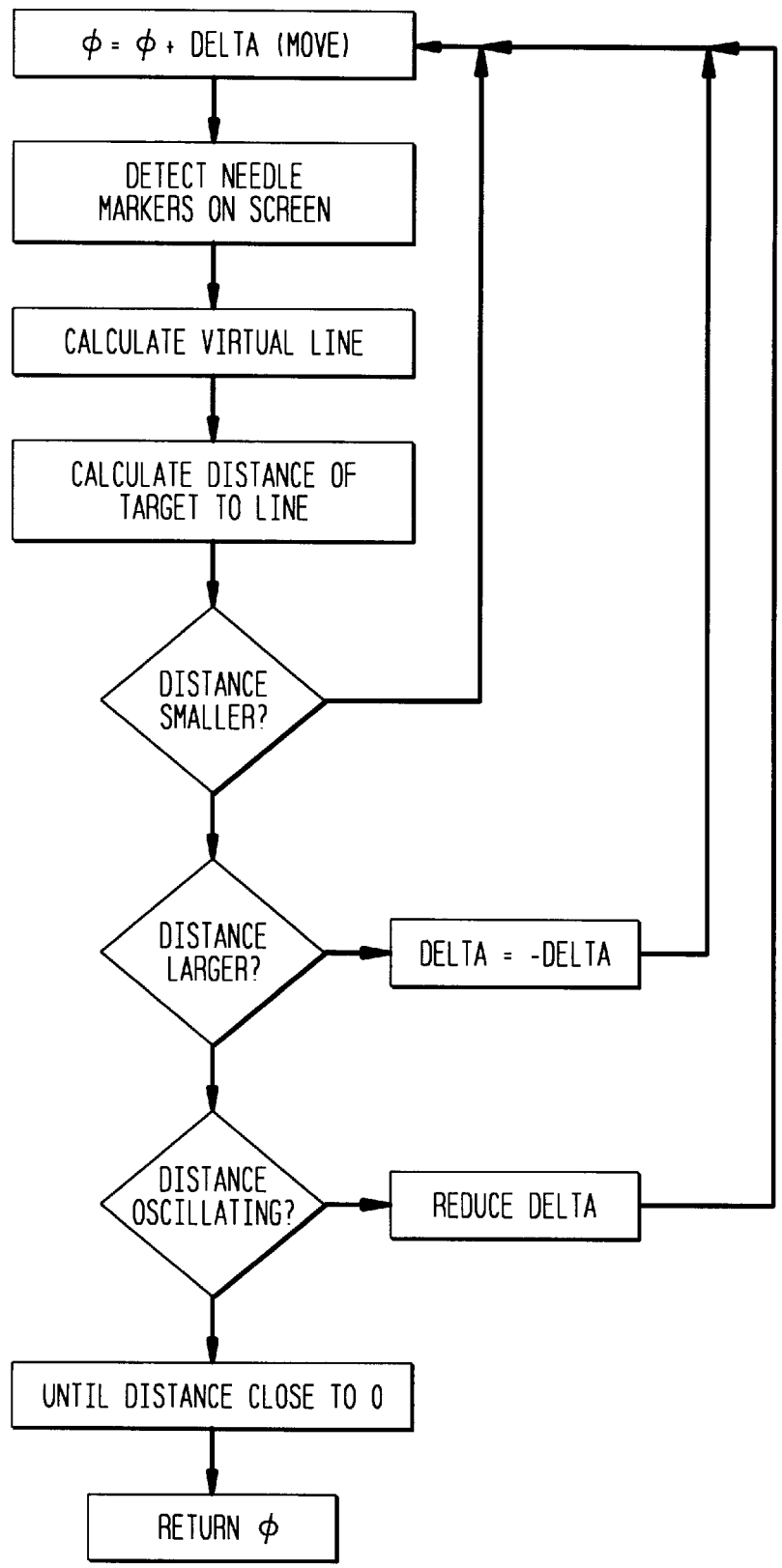
Figure 20:
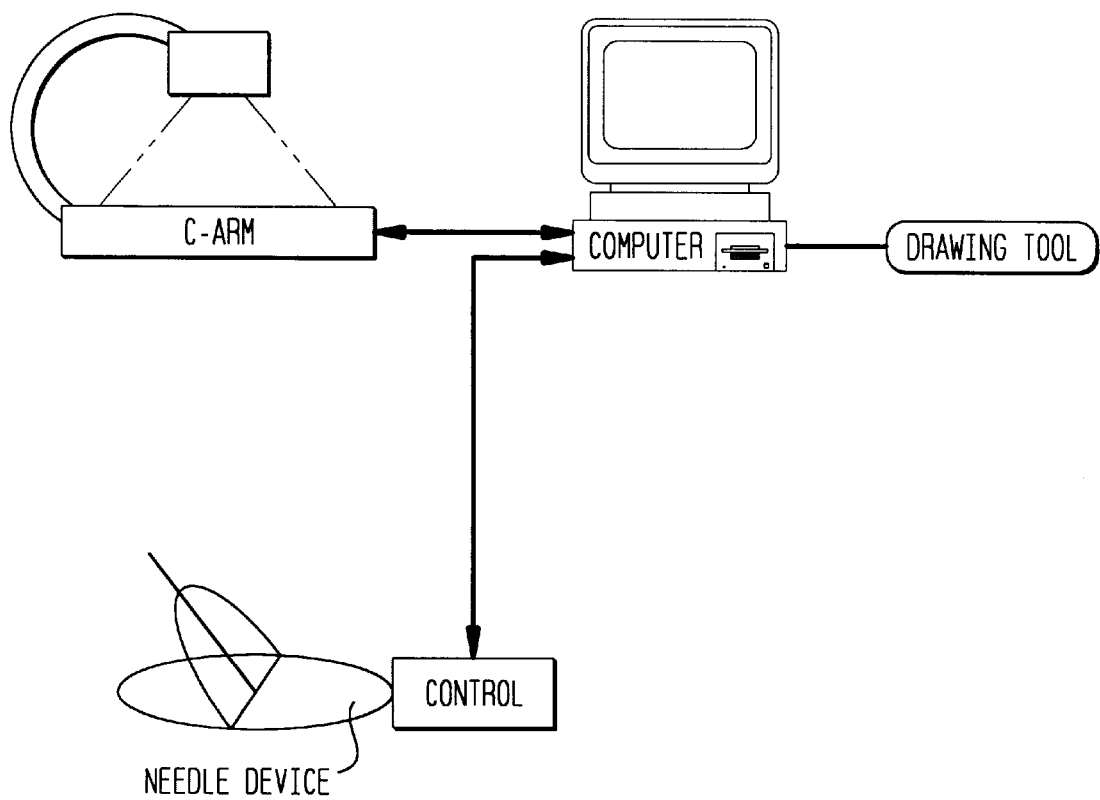
Figure 24:
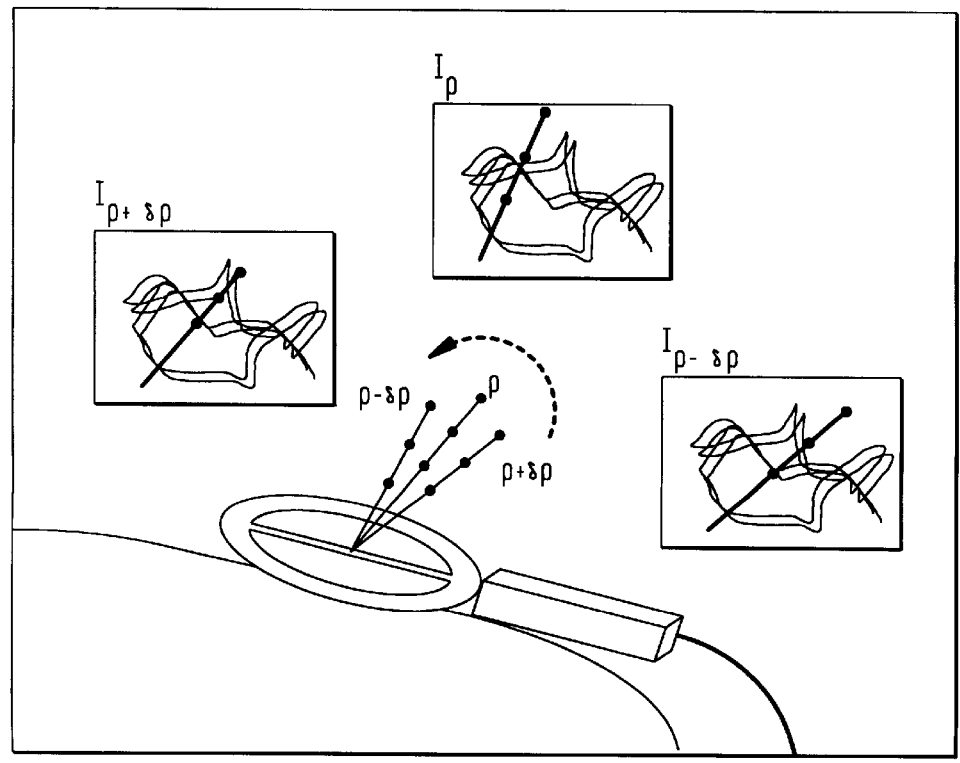
Figure 25:
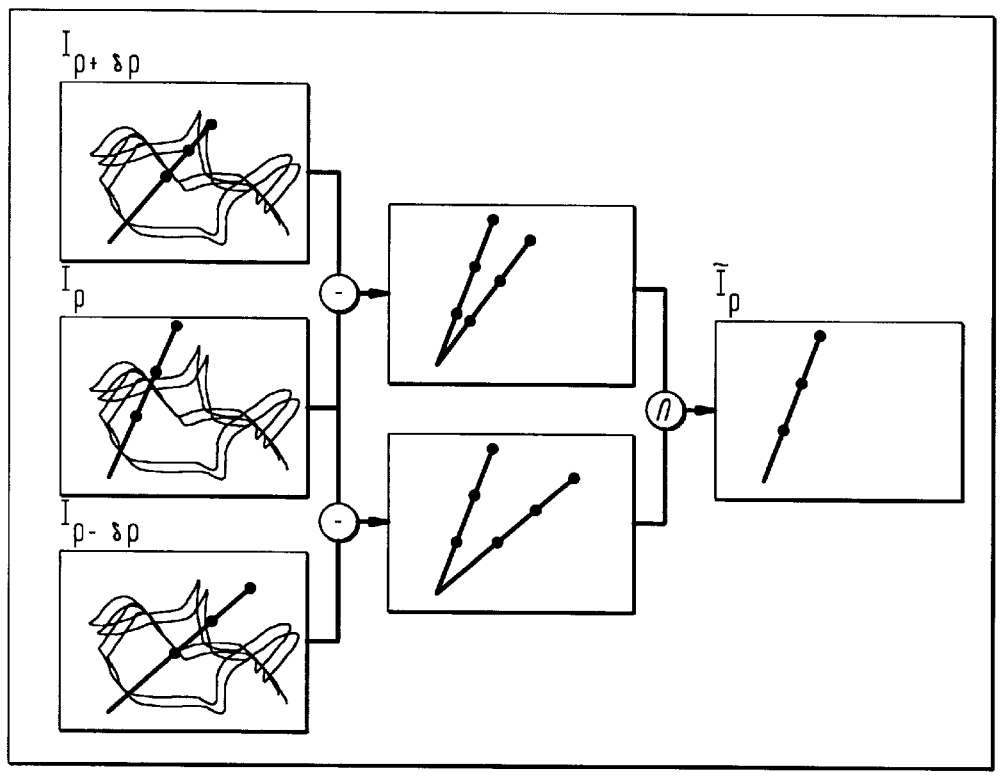

FIGS. 4, 5, and 6 show various steps of a method relating to the background and an example of a possible environment of the invention;

FIGS. 7 and 8 show diagrammatic representations of principles and apparatus relating to relating to the background and an example of a possible environment of the invention;

FIGS. 9, 10, and 11 show various steps of a method utilizable in conjunction with the invention;

FIGS. 12, 13, and 14 show diagramatically apparatus and principles relating to the background and an example of a possible environment of the invention;

FIG. 15 shows a system diagram relating to the background and an example of a possible environment of the invention;

FIG. 16 a diagrammatic representation of apparatus helpful to an understanding of the background and providing an example of a possible environment of the invention;

FIGS. 17, 18, and 19 show flow charts helpful to gaining an understanding of the background and an example of a possible environment of the invention;

FIG. 20 shows components of an automatic system and their interrelationship of a method utilizable in conjunction with the invention;

FIGS. 21, 22, 23, and 26 show diagrams in accordance with the principles of the invention; and FIGS. 24, and 25 show diagrammatic representations helpful to an understanding of the invention.

For a full and clear understanding of the present invention and the nature of the problem to which it is addressed, it is desirable to have a clear knowledge of the apparatus and method to which the invention applies. As stated above, this apparatus and method for determining the correct insertion depth for a biopsy needle are disclosed in the above patent applications.

Accordingly, it is appropriate to review in some detail the principles of construction and operation of the apparatus for determining the correct insertion depth for a biopsy needle as described in the apparatus and method for determining the correct insertion depth for a biopsy needle disclosed in the above patent application in the name of Navab et al.

Figure 1:
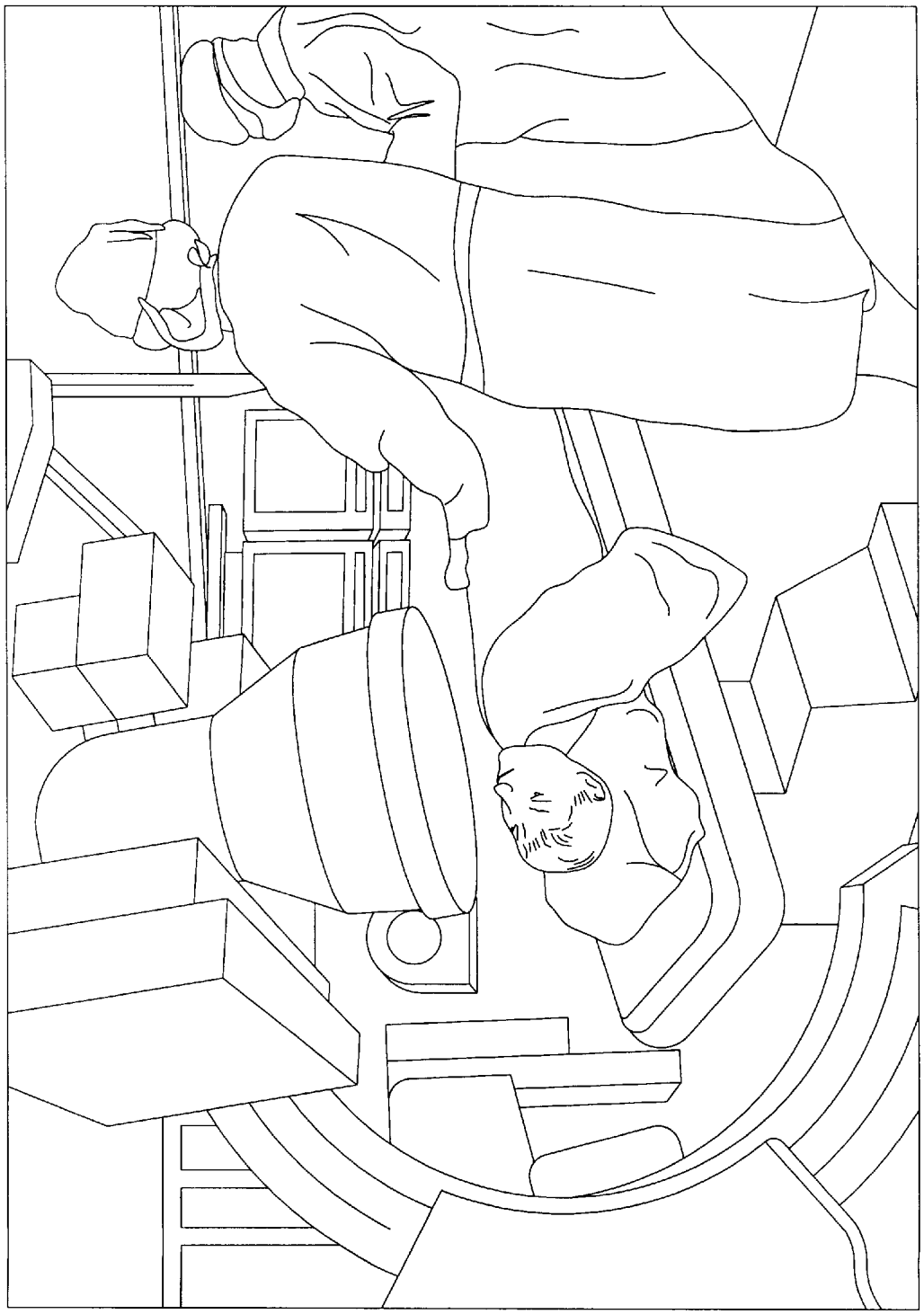
Figure 2:
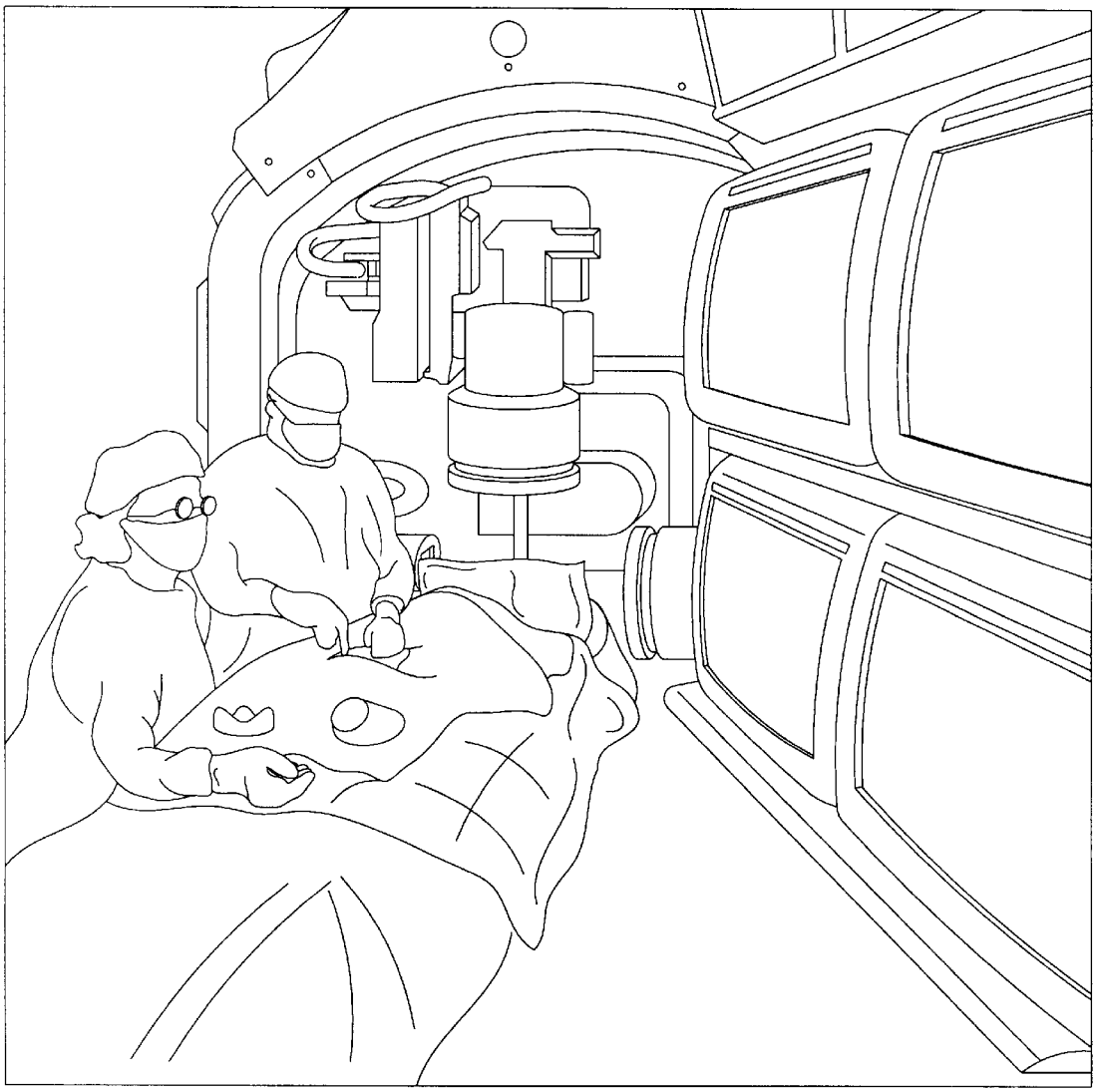
FIG. 2 shows a known type of fluoroscope with two simultaneous orthogonal views, such as may be utilized in conjunction with the present invention.
Figure 3:
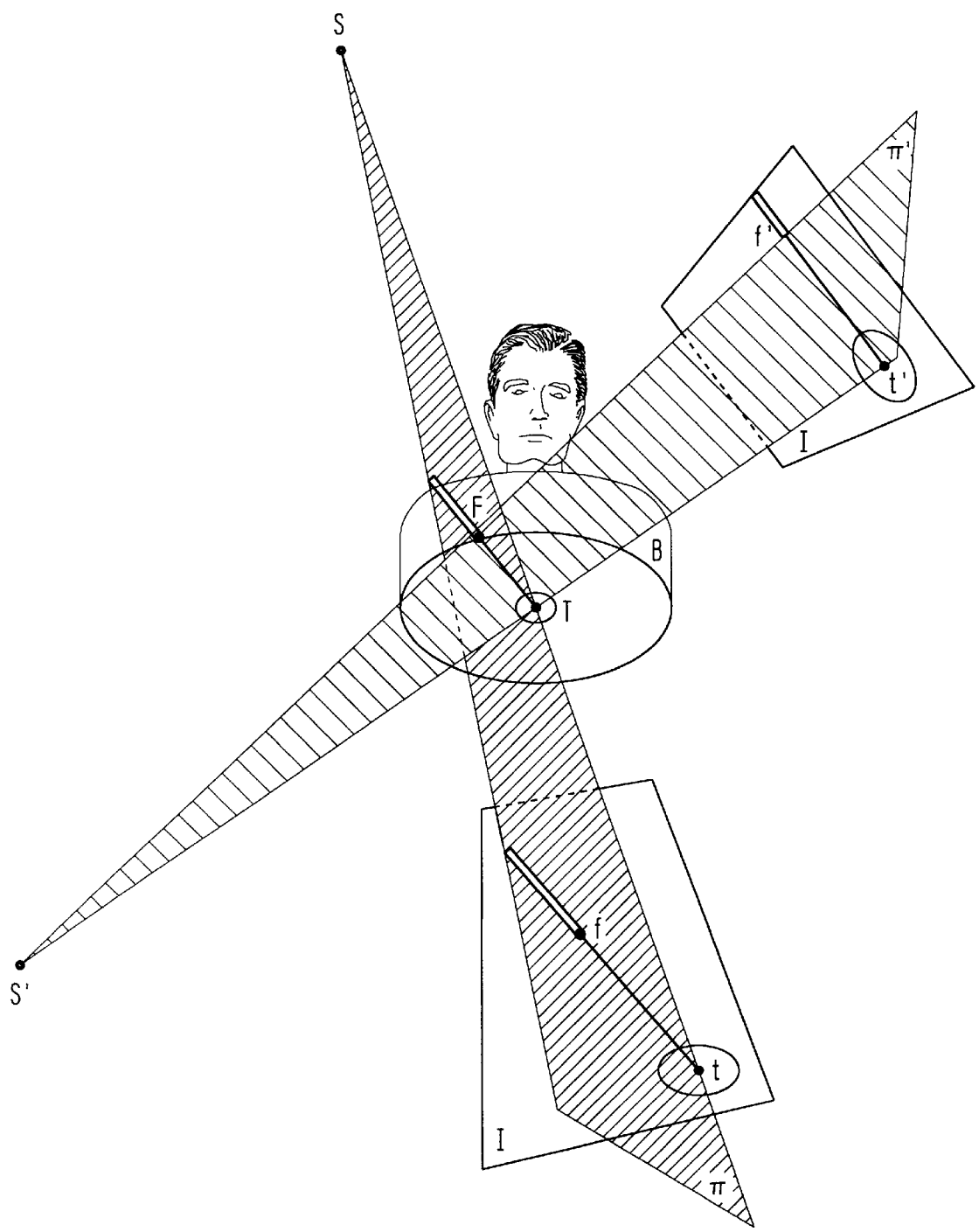
FIG. 3 shows a diagrammatic configuration of imaging radiation sources, image screens and a target area, relating to the background and an example of a possible environment of the invention.

FIG. 3 shows the geometry desirable for the surgeon. Preferably, the biopsy needle should be positioned such that its straight line continuation, or virtual extension, passes through a deep-seated target T inside the patient. During the manual procedure, the surgeon keeps the bottom end F of the needle on or near the patient's body and changes its direction until the virtual extension of the needle passes through the radiographic image t of the target T. The correct needle direction has to be verified on two radiographs that are taken from different angles.

As explained in the above-referenced patent application in the name of Navab et al., the apparatus has a geometrical configuration embodying a reasoned interpretation of what the surgeon seeks to do intuitively during a manual adjustment procedure. Clearly, the surgeon does not compute the exact or relative position and orientation of the C-arm and the image plane during a more or less refined "hit or miss" procedure. Rather, the surgeon proceeds by simple reasoning directly from radiographic images to the moving needle.

Referring again to FIG. 3, the imaging system, in accordance with the above-referenced patent application in the name of Navab et al. the apparatus for determining the correct insertion depth for a biopsy needle is modelled approximately as a "pinhole camera" model. The optical center, S, represents the location of the X-ray source and the position and orientation of an image intensifier defines the image plane, I. The deep-seated target inside patient's body is indicated by T, with t being its radiographic image.

F is a fixed point from where the surgeon wishes to insert the biopsy needle. f is its radiographic image. The viewing plane $\pi$ is defined by the optical center, S, the target on the image, t, and the fixed point, F, and its radiographic image, f.

All the entities and reference letters relating to a second position of the X-ray and therefore to a second radiographic image are noted by prime, such as S', $\pi$, and so on.

Generally, images of all lines lying on the plane $\pi$ which do not pass through the optical center S, are collinear to the line ft on the radiographic image I. Since the depth of the target T, or $\|FT\|$, is unknown, the maximum information that can be obtained on the position and orientation of the biopsy needle from a sequence of images taken from a single viewpoint is the three dimensional position of the plane $\pi$. Accordingly, a first part of the algorithm in accordance with the above-referenced patent application in the name of Navab et al. can be established, in accordance with the invention in Step I, as follows.

Any plane $\pi_1$ passing through the fixed point F, other than the plane $\pi$ itself, intersects the plane $\pi$ in one line. This line clearly contains the point F and therefore its image must pass through the image f of the fixed point F on the image on image plane I. The first two steps of the algorithm can now be defined, resulting in a method of accurately obtaining the three dimensional coordinates of the viewing plane $\pi$. A metallic, or other radiation-opaque, bar is rotated around the fixed point F in an arbitrary plane in passing through the fixed point F. See FIG. 4, which illustrates the step of finding a three-dimensional line lying on the viewing plane $\pi$. The shortest distance of the projection line of the three-dimensional line from the target t on the image is called $h_1$.

This $h_1$ distance decreases as the angle between them closes, and projection line approaches line $L_1$, representing the intersection of the planes $\pi$ and $\pi_1$, and vanishes at the intersection of these two planes. This provides a simple way to control the metallic bar under automatic images guidance and move it until it lies on the plane $\pi$.

In a further step, Step II, in accordance with the apparatus and method for determining the correct insertion depth for a biopsy needle, a metallic (X-ray opaque) bar is rotated around the fixed point F in a second plane $\pi$ passing through the fixed point F, and different from $\pi_1$, used in the Step I, see FIG. 5, which illustrates the procedure for finding a second three-dimensional line on the viewing plane $\pi$.

Preferably, the plane passing through F and orthogonal to $\pi_1$ is selected as $\pi_2$. The distance of its projection line from the target t on the image, is called $h_2$. This distance decreases as the projection line of $\pi_2$ approaches line $L_2$, representing the intersection of the planes $\pi$ and $\pi_2$ and this distance, $h_2$ vanishes at the intersection line of these two planes. This provides a way to control a second metallic bar under automatic images guidance and move it until it also lies on the plane $\pi$. Now two distinct lines, $L_1$ and $L_2$, having a non-zero angle of intersection therebetween, are identified on the plane $\pi$. These lines uniquely define the plane $\pi$ in three dimensional space. This is the maximum information that can be had from a single viewpoint with no calibration data.

A next step in accordance with the apparatus and method for determining the correct insertion depth for a biopsy needle disclosed in the above patent application to Navab et al., Step III, is the use of a second viewpoint. The radiographic image from a second viewpoint can be obtain either by moving the C-arm of the machine arbitrarily; the larger is the angle of rotation the more accurate is the resulting position and orientation of the needle.

The plane defined by the optical center, the X-ray source S' of the new configuration of the imaging system, the target T and the fixed point F is designated as $\pi'$, analogous to plane $\pi$ in the previous determination. See FIG. 6 which shows the procedure for finding the right orientation for the biopsy needle.

A metallic bar is rotated around the fixed point F in the plane $\pi$ obtained in step II. The distance of its projection line, 1', from the target t' on the image taken from the new viewpoint, is called h'. This distance decreases as one gets closer to the line L', representing the intersection of the planes $\pi$ and $\pi'$ and this distance vanishes at the intersection of these two planes.

This provides a way to control the metallic bar manually or automatically using image guidance and move it until the line FT is found. FT is the line of intersection of the two flat planes $\pi$ and $\pi'$ and it therefore represents a vector direction in space passing through the proposed fixed insertion point F and, when produced, through the target T. Now, the surgeon can be guided to the correct positioning of the biopsy needle. The next step in accordance with the invention, Step IV, is to let the surgeon know how deep the target T is inside the patient.

The cross ratio is a fundamental invariant of perspective projection. See, for example, O.D. Faugeras, Three-Dimensional Computer Vision: A Geometric Viewpoint; MIT Press, Cambridge, Mass; 1993. This invariant can be used here to accurately compute FT, the depth of the target inside patient's body. Referring to FIG. 7, consider the four points A, B, C, and D, on a line in space. The cross ratio of these four points can be defined as $$\frac{AB \times CD}{AC \times BD}.$$

The perspective projection of these four points on any plane and with respect to any projection center, for example {a,b,c,d} and {e,f,g,h} in FIG. 7 results in the same cross ratio between the projected points:

$$\frac{AB \times CD}{AC \times BD} = \frac{ab \times cd}{ac \times bd} = \frac{ef \times gh}{eg \times fh}$$

For the case of two markers, $M_1$ and $M_2$, on the metallic bar used in step III, such that $\|M_1F\|$ and $\|M_2F\|$ are accurately known, and $m_1'$ and $m_2'$, their radiographic images, are easily and accurately detectable, see FIG. 8. The assumptions made are reasonable and readily realized in practice. The cross ratio computed for the image points [m'1, m'2, f, t'] is the same as the cross ratio of the four points [$M_1$, $M_2$, F, T] in the three dimensional space. The positions of all these points other than T are known. FT is then computed from the following equation:

$$\|FT\| = \frac{\lambda \times \|M_1F\| \times \|M_2F\|}{\|M_1M_2\| - \lambda \times \|M_1F\|}$$

where 
$$\lambda = \frac{\left\|\frac{\|f't'\|}{m_{2'}t'}\right\|}{\frac{\|m_{1'}f'\|}{\|m_{1'}m_{2'}\|}}$$

The positioning in accordance with the apparatus and method for determining the correct insertion depth for a biopsy needle disclosed in the above patent application to Navab et al. is designed based on the algorithm disclosed above. FIGS. 12, 13, 14, and 16 show a design configuration in accordance with the invention. A part of the apparatus is a semi-circle that can rotate at least from 0 to 180 degrees around the center of a circular base. This rotation angle is designated by α in FIG. 12. This semi-circle has a second degree of freedom: it can also turn around its own baseline from 0 to 180 degrees. This rotation angle is designated by Θ in FIG. 12. A metallic bar can rotate on the plane defined by this semi-circle from 0 to 180 degrees. This rotation angle is noted by φ in FIG. 12. In accordance with the invention, this provides all that is required. All rotations can be done either by hand, by command, or automatically. The parallel or serial connection between a computer, such as a personal computer (PC), and a positioning device can guide the system based on the minimization of $h_1$, $h_2$ and h' on the radiographic images. Further details about the interactive and automatic process are provided in appendix-A and appendix-B.

FIGS. 9, 10, and 11 provide bridging information to facilitate an understanding of the relationship between the foregoing algorithm and the design herein described. These figures include some of the constructions shown in previous figures and are helpful to bridging the steps between the geometric principles forming a basis for the present invention and the practical apparatus and method herein disclosed.

FIG. 9 shows the procedure utilized in finding one three dimensional line lying on the viewing plane π. This comprises positioning the semi-circle at an arbitrary position to define a plane $π_1$ and then moving the metallic bar mounted on the semi-circle to a position where its image passes through f and t on the image. This process can be done automatically. The metallic bar is moved to minimize the distance $h_1$ on the image. This process is not time-consuming and is readily carried out in real time.

FIG. 10 shows Step II, the process of finding a second three dimensional line lying on the viewing plane π. This is similar to the previous step, but the semi circle has turned by an angle in the order 90 degrees around its based line defining a new plane $π_2$.

FIG. 11 shows Steps III & IV: Finding the right orientation of the biopsy needle and the depth of the target T inside the patient's body. This comprises positioning the semi-circle in the plane, π' defined by the metallic bar in steps I and II, and then rotating the metallic bar until its radiographic view from the new viewpoint passes through f' and t'. The center of the circular base, F, and the target inside patient's body, T, lie on the both planes π and π'. Their intersection is therefore FT the correct direction of the biopsy needle. The depth of the target, |FT|, can then be computed using the invariance of cross ratios by perspective projection; see the previous section on the geometrical description. The whole process, steps I through IV, can be done in real time and the surgeon can easily move the device and find the new orientation of the biopsy needle and depth of the target at any other contact point on the patient's body. This design lends itself readily to economical implementation.

The interactive system in accordance with the present invention has the advantage of being an independent unit which can be used together with any kind of X-ray fluoroscopes or C-arm imaging system and it needs no physical connections with the imaging system. The unit is entirely and readily portable. Furthermore, the operating surgeon has no radiation exposure at all during the search for the correct position.

FIG. 15 shows a protocol for the interactive system as herein described, in accordance with the invention. In this case the apparatus is fixed on the patient on top of the desired entry point defined by the surgeon. The surgeon works with the control device while looking at the radiographs and can be in the same room or in another room where the radiographic images can be observed without the surgeon's being exposed to the radiation.

These are the consecutive steps of the process in accordance with the apparatus and method for determining the correct insertion depth for a biopsy needle disclosed in the above patent application to Navab et al.:

A first plane is taken by fixing a α=0 and Θ=$Θ_1$. See FIG. 13. Note that $Θ_1$ is quite arbitrary. A user can choose this plane so as to maintain a clear view of the metallic bar. This can be done using the control buttons, $π_1$, +α, −α, +Θ and −Θ, as shown in FIG. 15.

The user then selects the proper angle φ by moving the metallic bar until its radiographic image passes through the target point. This can be done by using buttons +φ and −φ as in FIG. 15. The orientation of the metallic bar is then defined as:

$L_1 = [\sin(\phi_1)\sin(\theta_1), \sin(\phi_1)\cos(\theta_1), \cos(\phi_1)]]$

See FIG. 13. Note that $\Theta_2$ is also arbitrary. A user can choose this plane in order to have a clear view of the metallic bar. This can be done using the control buttons, $\pi_2$, $+\Theta$, and $-\Theta$, as in FIG. 15.

A user finds the right angle $\phi$ by moving the metallic bar until its radiographic image passes through the target point. This can be done by using buttons $+\phi$ and $-\phi$, as in FIG. 15. The orientation of the metallic bar is then defined as:

$L_2 = [\sin(\phi_2)\sin(\theta_2), \sin(\phi_2)\cos(\theta_2), \cos(\phi_2)]$

The final viewing plane (see FIG. 14) is then defined by $$\alpha = \arccos\left(\frac{n_y}{c}\sin(n_z)\right)$$

and $$\theta = -\arccos\left(\frac{c}{\|n\|}\right)\sin(n_x(\sin(\alpha)n_z + \cos(\alpha)n_y))$$

where $$n = L \wedge L'$$

and $$c = \sqrt{(L_xL'_z - L_zL'_x)^2 + (L_yL'_x - L_xL'_y)^2}$$

and ^ is the vector product defined in $R^3$.

The system will automatically move to the right position and the user has no need to adjust $\Theta$ and $\alpha$ in this case.

The user then uses the image on the second image intensifier or moves the C-arm to a new position.

The user finds the proper angle $\phi$ by moving the metallic bar until its radiographic images passes through the target point. This can be done by using buttons $+\phi$ and $-\phi$ as shown in FIG. 15. This is the correct orientation of the needle to be used for the biopsy.

In order to compute the depth of the target in this case, two other auxiliary needles are placed on the base line of the semi-circle; see FIG. 16. In order not to disturb the image of the main needle, these needles can be made in acrylic (transparent to X-ray) with only a few metallic markers to be aligned with the deep seated target. The determination of depth is arrived at by a process of triangulation in which a base-line forms the base of a triangle with the directions of the other two sides of the triangle being determined by respective angles subtended by the base and the respective side. Accordingly, the accuracy is grater where the angle between a needle and the metallic bar is treater. Hence, two alternative needles are provided so that needle is utilized which is on the side of the obtuse angle made by the metallic bar with the plane of the diameter of the semicircle.

Each of these needles can rotate in the plane defined by this semi-circle around a fixed point other than the entry point. In accordance with the present embodiment, the two end points of the base line are used as the two centers of rotation. In the final position, the plane defined by the semi-circle also includes the deep seated target.

Once the correct orientation of the needle is found, the system activates that one of the auxiliary needles which has the greater angle with the main needle. The user moves this needle to align it with the target on the image. The system computes the depth of the target by computing the distance between the entry point and the intersection of the main needle and the active auxiliary needle. FIG. 16 shows this construction in detail.

The depth to the target, AC, is given by the trigonometric formula $$AC = \sin(\phi_1) \times \frac{AB}{\sin(\phi_1 - \phi)}$$

FIG. 17 shows a flowchart of the interactive process in accordance with the principles of the apparatus and method for determining the correct insertion depth for a biopsy needle disclosed in the above patent applications in the names of Navab and Geiger.

A semi-automatic system in accordance with the invention reduces the human interaction to the initial fixation of the unit on the patient, a definition, such as a manual definition, of the tumor on a computer display, and the final insertion of the needle, that will remain fully under the control of the surgeon.

The search for the optimal needle position and the calculation of the target depth is done automatically. The benefits of such a system are substantially increased speed of operation and thus less patient discomfort, reduced risk of patient motion, reduced radiation for the patient, and complete elimination of radiation for the surgeon during the search for the position.

The automatic system utilizes as a starting point the same basic arrangement as the manual version with additional features. Three effectors are included, such as drive motors, to change the needle position. One each is utilized for $\Theta$, one for $\phi$, and one for the rotation $\alpha$, respectively. X-ray opaque markers are provided on the biopsy needle guidance so as to be visible on the fluoroscopic images and to be readily detectable by an image processing unit.

A computer is linked to the fluoroscope so as to be able to capture and store the X-ray images and to perform the necessary image processing to detect the needle markers. A computer stores and calculates needle positions and commands the effectors so as to move the needle position. Furthermore, a user interface to the computer allows the surgeon to draw the outline of the target on the fluoroscopy image with a computer "mouse" coordinate translator or by using a graphics tablet.

Essentially, the procedure is as follows apparatus and method for determining the correct insertion depth for a biopsy needle disclosed in the above patent applications in the names of Navab and Geiger. The unit is installed on the patient. One single image from the fluoroscope is stored and displayed on the computer screen. The surgeon outlines manually the tumor on this image using the mouse. During this stage of the interaction, the fluoroscope is turn off, thereby reducing radiation exposure. The computer selects a first plane $\Theta$ and performs a task that is known as visual servoing. See FIG. 18. It changes the needle position, thereby varying $\phi$ and detects the needle markers on the fluoroscopic image. From the markers, it can determine the projection of the needle, that is the axial center-line of the needle produced or continued beyond the needle.

The closest distance of this "virtual needle" to the target in the image can be calculated. The position of the needle is changed until this distance is reduced to a minimal amount and the projection of the needle passes through the target. The parameters $\Theta$ and $\phi$ of the needle position are stored. This step is repeated for a different choice of $\Theta$ in order to find a second needle position. Then the C-arm position has to be changed, and the target must be outlined once again on a first image. From the two previous needle positions, the computer calculates the necessary rotations $\alpha$ and $\Theta$ to bring the needle in the final plane.

Then the visual servoing step is repeated. The final position φ is the one that passes through the target. The needle guidance system has to be blocked in that position, either using the effectors or by actuating an additional blocking or position locking device. The fluoroscopy unit is switched on for two initial images that are used for outlining the target, and during the visual servoing steps. This procedure is usually very brief. The system then uses the needle markers in order to automatically compute the depth of the target from the entry point. Depending on the speed of the effectors, the described system is able to find the optimal needle position and the depth of the target in a few seconds. FIG. 19 shows a flowchart of this automatic process. FIG. 20 shows the connection and relationship between the different components of the automatic system.

It is clear from the foregoing that any uncertainty or error in the identification of the location of the image-opaque metallic markers incorporated in the needles is reflected by errors in the alignment of the needle and the deep-seated target, and the depth determination as performed in accordance with the foregoing apparatus and method. As was noted above, in performing the method, it is important for the surgical practitioner to be able to obtain correct reading of the depth to which insertion is required and, to this end, it is necessary to be able to identify positively the surgical tool or device and image-opaque markers placed upon it in order to obtain the necessary data for accurate alignment of the needle and the deep-seated target, and depth determination. It is particularly difficult to make such identification of a surgical tool, such as a biopsy needle or other device, when the needle or device is overlaid with anatomical background as is so often the case in radiographic images on the screen of a fluoroscope or other imaging device.

In accordance with the present invention, visual servoing, and therefore the active control, of a positioning device can give a simple but precise solution to the difficult problem of detection of markers or instruments overlaid with anatomical background in radiographic images.

A set of consecutive images is utilized in order to detect and track the positioning device in accordance with the present invention. As with all imaging techniques which utilize the relationship between consecutive images in a sequence of images, patient movement should be kept to a minimum. Accordingly, the present invention allows the utilization of a time interval between such images that is short enough so that any patient motion can be considered to be negligibly small and thus can be neglected in the determination.

The method in accordance with the present invention, utilizes subtraction and intersection of consecutive images in order to segment out the active parts of the positioning device and thereby obviates any need to search whole images full of anatomical features in order to find the positioning device.

The apparent motion of the active device, such as a needle or a set of imbedded ball bearings or other image-opaque markers, should preferably be such that the difference permits the device to be seen in two different positions in each of the subtracted images. The presence of the object of interest in the subtracted images can be checked for automatically. In the case where the objects overlap a larger motion is applied or time interval between two consecutive image acquisition is increased.

Figure 21:
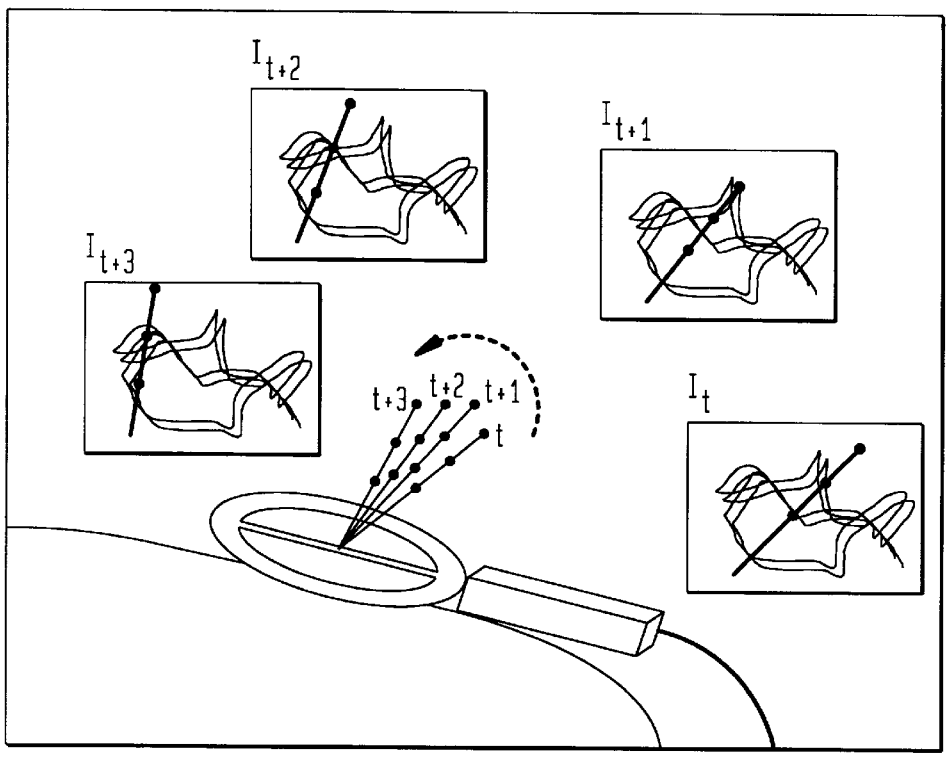
Figure 22:
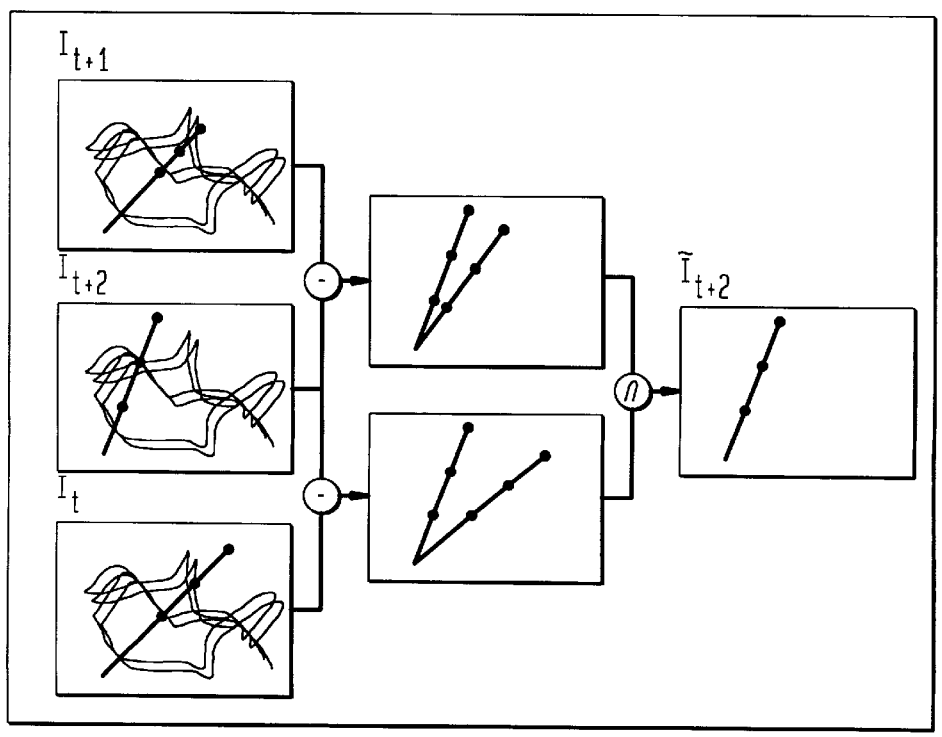
Figure 23:
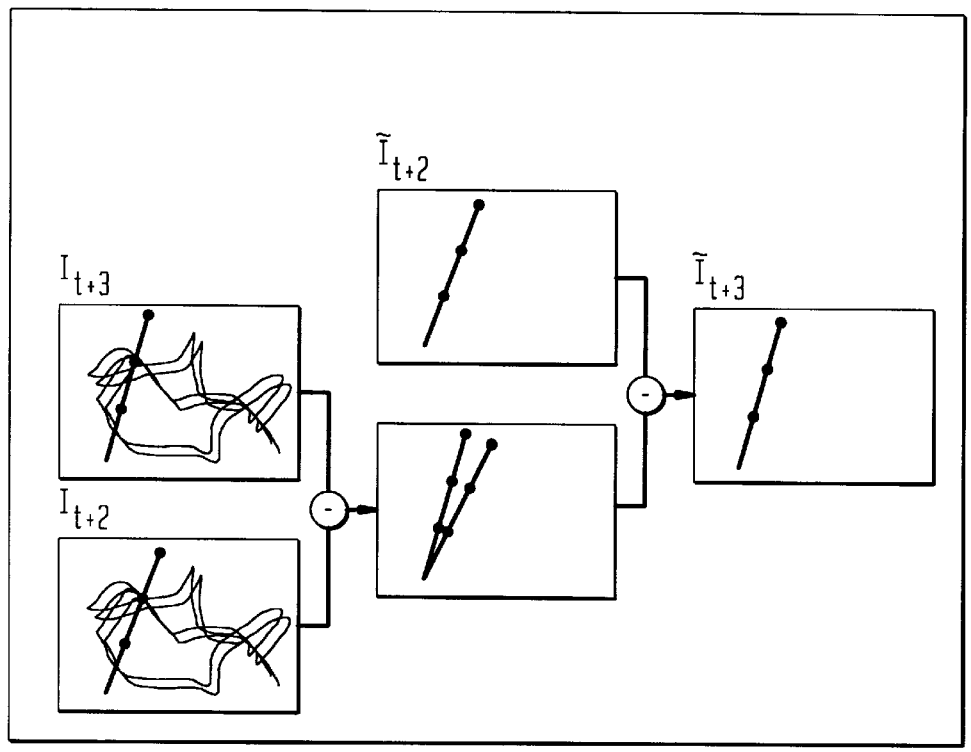

Thus suppose that the device is moving and a set of X-ray images are taken at times t, t+1, and t+3, as in FIG. 21. In order to detect the device in the image $I_{t+2}$, taken at time t+2, these detect are subtracted from the images taken at time t,
and t+1. This results in two difference images ($I_{t+2}-I_{t+1}$), and ($I_{t+2}-I_{t}$). If the motion between the two frames is such that the images of the device are distinct while the background is static, these difference images contain only the images of the active, moving device after and before the motion between the two frames. Therefore the mathematical intersection of these two difference images ($I_{t+2}-I_{t+1}$), and ($I_{t+2}-I_{t}$) leads to the full detection of the device on the image $I_{t+2}$. See FIG. 22.

Once the device is detected and extracted on an image, for example, $I_{t+2}$, the device can be detected in the next image, for example, $I_{t+3}$, using only these two images, $I_{t+2}$ and $I_{t+3}$. This is carried out by first subtracting the two images $I_{t+2}$ and $I_{t+3}$, and then by taking out the previously detected image of the device on $I_{t+2}$ from this difference image $I_{t+2}-I_{t+3}$. See FIG. 23.

Where there is need to detect the device when it is not in motion, the above principle is still applicable by applying a small vibration, perturbation, or local motion to the device and taking the intersection of the difference images between the last image, and all other images taken during the applied motion. This allows detection of the device despite a "busy" anatomical background which creates problem for all classical image processing algorithms which try to detect an object of interest in a cluttered static scene.

In FIG. 24, a surgical tool or device is at a position p and the system moves it to a different position by vibrating the device. At least two images are required while the device is in motion. Thus, suppose that the device is at positions p+δp and p−δp when these two "shots" are taken. FIG. 25 illustrates the method for detecting the device at position p on the image. This detection technique is essentially similar to that described above for the images $I_t$, $I_{t+1}$, and $I_{t+2}$, taken during device motion.

In order to detect the device on an image $I_p$, taken when the device is at a given position p, the device is moved or vibrated to at least two other positions p+δp and p−δp. In order to detect the device in the image $I_p$, this image is subtracted from the images $I_{p+\delta p}$ and $I_{p-\delta p}$ taken during the vibration. This provides two difference images ($I_p-I_{p+\delta p}$) and ($I_p-I_{p-\delta p}$). If the motion between the two frames is such that the images of the device are distinct while the background is static, these difference images contain only the images of the active device after and before the vibration. Therefore the intersection of these two difference images ($I_p-I_{p+\delta p}$) and ($I_p-I_{p-\delta p}$). See FIG. 25.

It is noted that a displacement of the positioning device in the plane passing through the X-ray source and position p may result in a small motion of the device, thereby causing imprecise detection. However, this can be automatically verified if, for example, the device includes n balls, of steel or other image-opaque material, then 2*n balls have to be visible in the difference image. As the user has the power to move the device freely, the device is in this instance simply moved to another plane, for example, into a plane that is orthogonal to the original plane.

Formally, the method in accordance with the invention comprises the following steps:

generate a radiographic reference image $I_p$, including an image of a surgical device and an anatomical background image;

apply an oscillating movement to the device;

generate a number k of radiographic images $I_k$ during the oscillating movement;

subtract each image $I_k$ from the reference image $I_p$ so as to generate a difference image ($I_k-I_p$);

derive the mathematical intersection of all of the reference images ($I_k-I_p$); and thereby obtain a resulting image containing only the image of the device on the radiographic reference image $I_p$ without the anatomical background image.

It is noted that more images of the device during this motion would provide redundant data and therefore lead to a better detection result. If more than three images are taken during the process of vibration, then the difference of each of these images with the images taken after vibration can be taken in the final position $I_p$, and then the intersection of all of these difference images taken. At least two of these difference images are needed, as shown in FIGS. 24 and 26.

The rate at which the vibration or oscillation takes place depends on the performance capability of the imaging apparatus and so cannot be generally stated. However, the criterion is simple: the rate should be sufficiently slow such that images do not become blurred with the imaging apparatus being used.

Figure 26:
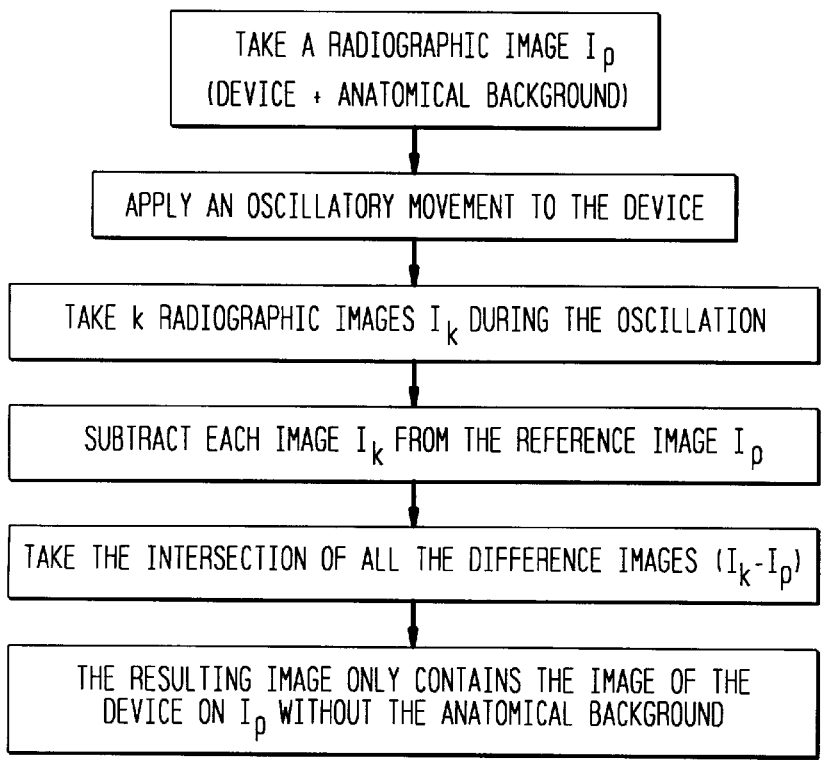

The flow chart in FIG. 26 shows the algorithm for detecting this active device using the above method.

While the invention has been described in terms of exemplary embodiments, it will be apparent to one of skill in the art to which it pertains that various changes and modifications can be implemented without departing from the spirit of the invention whose scope is defined by the claims following. It will also be understood that the use of a programmable computer to implement various functions is contemplated.

What is claimed is:

1. A method for detection and localization of a surgical tool in a radiographic image, comprising the steps of:

generating a radiographic reference image $I_p$, including an image of a surgical device and an anatomical background image;

applying an oscillating movement to said device;

generating a number k of radiographic images $I_k$ during said oscillating movement;

subtracting each image $I_k$ from a preceding reference image $I_p$ so as to generate a difference image $(I_k-I_p)$; and deriving said mathematical intersection of all of said reference images $(I_k-I_p)$, whereby a resulting image results including only said image of said device on said radiographic reference image $I_p$ and substantially without said anatomical background image.

2. A method for detection and localization of a surgical tool in a radiographic image, in accordance with claim 1, wherein said steps of subtracting each image $I_k$ from said reference image $I_p$ and of deriving said mathematical intersection are performed on digitized versions of said respective images.

3. A method for detection and localization of a surgical tool in a radiographic image, in accordance with claim 1, wherein said step of generating a radiographic reference image $I_p$, including an image of a surgical device is carried out on a biopsy needle.

4. A method for detection and localization of a surgical tool in a radiographic image in accordance with claim 1, wherein said step of applying an oscillating movement $I_k$ to said device is performed no faster than a rate at which acquisition can be effected of two successive distinct radiographic images of said surgical tool.

5. A method for detection and localization of a positioning device in a radiographic image in the presence of anatomical background images, comprising the steps of:

generating a radiographic reference image $I_p$, including an image of said positioning device and an anatomical background image;

applying an oscillating movement to said device;

generating a number k of radiographic images $I_k$ during said oscillating movement;

subtracting each image $I_k$ from a preceding reference image $I_p$. so as to generate a difference image $(I_k-I_p)$; and deriving said mathematical intersection of all of said reference images $(I_k-I_p)$, whereby a resulting image results including only said image of said device on said radiographic reference image $I_p$ and substantially without said anatomical background image.

6. A method for detection and localization of a surgical tool in a radiographic image, in accordance with claim 5, wherein said steps of subtracting each image $I_k$ from said reference image $I_p$ and of deriving said mathematical intersection are performed on digitized versions of said respective images.

7. A method for detection and localization of a surgical tool in a radiographic image, in accordance with claim 5, wherein said step of generating a radiographic reference image $I_p$, including an image of a surgical device is carried out on a biopsy needle.

8. A method for detection and localization of a surgical tool in a radiographic image in accordance with claim 5, wherein said step of applying an oscillating movement $I_k$ to said device is performed no faster than a rate at which acquisition can be effected of two successive distinct radiographic images of said surgical tool.

9. A method for tracking a positioning device in a sequence of consecutive radiographic images, said positioning device exhibiting a change of position from one radiographic image to the next, said method comprising the steps of:

generating a radiographic reference image $I_p$, including an image of a positioning device and an anatomical background image;

applying an oscillating movement to said device;

generating a number k of radiographic images $I_k$ during said oscillating movement;

subtracting each image $I_k$ from a preceding reference image $I_p$ so as to generate a difference image $(I_k-I_p)$; and deriving said mathematical intersection of all of said reference images $(I_k-I_p)$, whereby a resulting image results including only said image of said device on said radiographic reference image $I_p$ and substantially without said anatomical background image.

10. A method for detection and localization of a surgical tool in a radiographic image, in accordance with claim 9, wherein said steps of subtracting each image $I_k$ from said reference image $I_p$ and of deriving said mathematical intersection are performed on digitized versions of said respective images.

11. A method for detection and localization of a surgical tool in a radiographic image, in accordance with claim 9, wherein said step of generating a radiographic reference image $I_p$, including an image of a surgical device is carried out on a biopsy needle.

12. A method for detection and localization of a surgical tool in a radiographic image in accordance with claim 9, wherein said step of applying an oscillating movement $I_k$ to said device is performed no faster than a rate at which acquisition can be effected of two successive distinct radiographic images of said surgical tool.

13. Apparatus for detection and localization of a positioning device in a radiographic image in the presence of anatomical background images, comprising:

means for generating a radiographic reference image $I_p$, including an image of said positioning device and an anatomical background image;

means for applying an oscillating movement to said device;

means for generating a number k of radiographic images $I_k$ during said oscillating movement;

means for subtracting each image $I_k$ from a preceding reference image $I_p$ so as to generate a difference image $(I_k-I_p)$; and means for deriving said mathematical intersection of all of said reference images $(I_k-I_p)$, whereby a resulting image results including only said image of said device on said radiographic reference image $I_p$ and substantially without said anatomical background image.

14. Apparatus for tracking a positioning device in a sequence of consecutive radiographic images, said positioning device exhibiting a change of position from one radiographic image to the next, said apparatus comprising:

means for generating a radiographic reference image $I_p$, including an image of a positioning device and an anatomical background image;

means for applying an oscillating movement to said device;

means for generating a number k of radiographic images $I_k$ during said oscillating movement;

means for subtracting each image $I_k$ from a preceding reference image $I_p$ so as to generate a difference image $(I_k-I_p)$; and means for deriving said mathematical intersection of all of said reference images $(I_k-I_p)$, whereby a resulting image results including only said image of said device on said radiographic reference image $I_p$ and substantially without said anatomical background image.

15. Apparatus for detection and localization of a surgical tool in a radiographic image, for use in conjunction with radiographic equipment or the like imaging equipment, said apparatus comprising:

means for applying an oscillating movement to said device;

means for generating a radiographic reference image $I_p$, including an image of a surgical device and an anatomical background image, and for generating a number k of radiographic images $I_k$ during said oscillating movement;

means for subtracting each image $I_k$ from a preceding reference image $I_p$ so as to generate a difference image $(I_k-I_p)$; and means for deriving said mathematical intersection of all of said reference images $(I_k-I_p)$.

16. Apparatus for detection and localization of a surgical tool in a radiographic image, as recited in claim 15 wherein said means for subtracting each image $I_k$ from said reference image $I_p$ and of deriving said mathematical intersection utilizes digitized versions of said respective images.

17. Apparatus for detection and localization of a surgical tool in a radiographic image, as recited in claim 15, wherein said image of a surgical device is an image of a biopsy needle.

18. Apparatus for detection and localization of a surgical tool in a radiographic image, as recited in claim 15, wherein said means for applying an oscillating movement to said device causes said oscillating movement to be at a rate no faster than a rate that allows unblurred images to be made.

* * * * *